(12) United States Patent
Ho

(10) Patent No.: US 12,067,225 B2
(45) Date of Patent: Aug. 20, 2024

(54) DEVICES, SYSTEMS, AND METHODS TO EMPHASIZE REGIONS OF INTEREST ACROSS MULTIPLE IMAGING MODALITIES

(71) Applicant: Canon USA, Inc., Melville, NY (US)

(72) Inventor: Christina Ho, Brookline, MA (US)

(73) Assignee: Canon U.S.A., Inc., Melville, NY (US)

( * ) Notice: Subject to any disclaimer, the term of this patent is extended or adjusted under 35 U.S.C. 154(b) by 132 days.

(21) Appl. No.: 16/401,390

(22) Filed: May 2, 2019

(65) Prior Publication Data
US 2019/0339850 A1 Nov. 7, 2019

Related U.S. Application Data

(60) Provisional application No. 62/666,252, filed on May 3, 2018.

(51) Int. Cl.
*G06F 3/00* (2006.01)
*A61B 5/00* (2006.01)
(Continued)

(52) U.S. Cl.
CPC ........ *G06F 3/04847* (2013.01); *A61B 5/0066* (2013.01); *A61B 5/0071* (2013.01);
(Continued)

(58) Field of Classification Search
CPC ............ G06F 3/04847; G06F 3/04845; G06F 3/0485; G06F 3/04883; G06F 2203/04808;
(Continued)

(56) References Cited

U.S. PATENT DOCUMENTS 5,357,550 A 10/1994 Asahina et al.
6,565,514 B2 5/2003 Svanerudh et al.
(Continued)

FOREIGN PATENT DOCUMENTS

JP 2016-508750 A 3/2016
WO 2015/045368 A1 4/2015
(Continued)

OTHER PUBLICATIONS

Tearney, G. J., "Spectrally encoded miniature endoscopy", Optics Letters, vol. 27, No. 6, Mar. 15, 2002, pp. 412-414.
(Continued)

*Primary Examiner* — Kieu D Vu
*Assistant Examiner* — Anita D Chaudhuri
(74) *Attorney, Agent, or Firm* — Canon U.S.A., Inc. IP Division

(57) ABSTRACT

One or more devices, systems, methods and storage mediums for optical imaging medical devices, such as, but not limited to, Optical Coherence Tomography (OCT), single mode OCT, and/or multi-modal OCT apparatuses and systems, and methods and storage mediums for use with same, for viewing, controlling, updating, and emphasizing multiple imaging modalities are provided herein. One or more embodiments provide at least one intuitive Graphical User Interface (GUI), method, device, apparatus, system, or storage medium to comprehend information, including, but not limited to, molecular structure of a vessel, and to provide an ability to manipulate the vessel information. In addition to controlling multiple imaging modalities, the GUI may operate for one or more applications, including, but not limited to, expansion/underexpansion (e.g., for a stent) and/or apposition/malapposition (e.g., for a stent), co-registration and imaging.

27 Claims, 18 Drawing Sheets

(51) Int. Cl.
    *G06F 3/04845*     (2022.01)
    *G06F 3/04847*     (2022.01)
    *G06F 3/0485*     (2022.01)
    *G06F 3/04883*     (2022.01)
    *G06F 9/00*     (2018.01)
    *G06F 17/00*     (2019.01)

(52) U.S. Cl.
    CPC .......... *A61B 5/7425* (2013.01); *A61B 5/7435* (2013.01); *A61B 5/748* (2013.01); *G06F 3/04845* (2013.01); *G06F 3/0485* (2013.01); *G06F 3/04883* (2013.01); *G06F 2203/04808* (2013.01)

(58) Field of Classification Search
    CPC ... A61B 5/0066; A61B 5/0071; A61B 5/7425; A61B 5/7435; A61B 5/748; A61B 6/469; A61B 6/5247; A61B 5/0084; A61B 5/0035
    See application file for complete search history.

(56) References Cited

U.S. PATENT DOCUMENTS

| | | |
|---|---|---|
| 6,763,261 B2 | 7/2004 | Casscells, III et al. |
| 7,366,376 B2 | 4/2008 | Shishkov et al. |
| 7,414,779 B2 | 8/2008 | Huber et al. |
| 7,796,270 B2 | 9/2010 | Yelin et al. |
| 7,843,572 B2 | 11/2010 | Tearney et al. |
| 7,872,759 B2 | 1/2011 | Tearney et al. |
| 7,889,348 B2 | 2/2011 | Tearney et al. |
| 7,916,387 B2 | 3/2011 | Schmitt |
| 7,930,014 B2 | 4/2011 | Huennekens et al. |
| 7,978,916 B2 | 7/2011 | Klingensmith et al. |
| 8,289,522 B2 | 10/2012 | Tearney et al. |
| 8,315,282 B2 | 11/2012 | Huber et al. |
| 8,325,419 B2 | 12/2012 | Schmitt |
| 8,412,312 B2 | 4/2013 | Judell et al. |
| 8,478,387 B2 | 7/2013 | Xu |
| 8,493,567 B2 | 7/2013 | Inoue |
| 8,581,643 B1 | 11/2013 | Schmitt |
| 8,676,013 B2 | 3/2014 | Bouma et al. |
| 8,909,323 B2 | 12/2014 | Baumgart |
| 8,928,889 B2 | 1/2015 | Tearney et al. |
| RE45,534 E | 6/2015 | Huennekens et al. |
| 9,087,368 B2 | 7/2015 | Tearney et al. |
| 9,121,926 B2 | 9/2015 | Nair et al. |
| 9,138,147 B2 | 9/2015 | Schmitt et al. |
| 9,173,591 B2 | 11/2015 | Elbasiony et al. |
| 9,207,064 B2 | 12/2015 | Inoue |
| 9,286,673 B2 | 3/2016 | Begin et al. |
| 9,292,918 B2 | 3/2016 | Zagrodsky et al. |
| 9,295,450 B2 | 3/2016 | Furuichi et al. |
| 9,301,687 B2 | 4/2016 | Kemp |
| 9,307,926 B2 | 4/2016 | Begin et al. |
| 9,332,942 B2 | 5/2016 | Jaffer et al. |
| 9,349,178 B1* | 5/2016 | Itu .......... A61B 6/507 |
| 9,351,698 B2 | 5/2016 | Dascal et al. |
| 9,462,950 B2 | 10/2016 | Xu |
| 9,557,154 B2 | 1/2017 | Tearney et al. |
| 10,109,058 B2 | 10/2018 | Ambwani et al. |
| 10,288,868 B2 | 5/2019 | Tearney et al. |
| 2010/0092389 A1 | 4/2010 | Jaffer et al. |
| 2010/0106240 A1* | 4/2010 | Duggal ............ A61B 17/12118 623/1.15 |
| 2011/0292400 A1 | 12/2011 | Fleming et al. |
| 2012/0101374 A1 | 4/2012 | Tearney et al. |
| 2012/0172700 A1* | 7/2012 | Krishnan ............... G16H 30/20 600/407 |
| 2013/0123616 A1 | 5/2013 | Merritt et al. |
| 2014/0270436 A1 | 9/2014 | Dascal et al. |
| 2014/0276011 A1 | 9/2014 | Schmitt et al. |
| 2015/0250438 A1 | 9/2015 | Bozkaya et al. |
| 2015/0272442 A1 | 10/2015 | Motafakker-fard et al. |
| 2016/0171711 A1 | 6/2016 | Gopinath et al. |
| 2016/0228097 A1 | 8/2016 | Jaffer et al. |
| 2016/0335766 A1* | 11/2016 | Ambwani ............ G06K 9/4647 |
| 2017/0010352 A1 | 1/2017 | Liu et al. |
| 2017/0020392 A1 | 1/2017 | Xu |
| 2017/0024532 A1 | 1/2017 | Gopinath et al. |
| 2017/0103520 A1 | 4/2017 | Gopinath et al. |
| 2017/0135584 A1 | 5/2017 | Tearney et al. |
| 2017/0164931 A1 | 6/2017 | Ng et al. |
| 2017/0169566 A1* | 6/2017 | Lu .......................... G06T 7/0012 |
| 2017/0209049 A1* | 7/2017 | Wang .................... A61B 5/0071 |
| 2019/0099080 A1 | 4/2019 | Kunio et al. |
| 2019/0102906 A1 | 4/2019 | Kunio et al. |

FOREIGN PATENT DOCUMENTS

| | | |
|---|---|---|
| WO | 2016/015052 A1 | 1/2016 |
| WO | 2016/094909 A1 | 6/2016 |
| WO | 2016/144878 A1 | 9/2016 |
| WO | 2016/187231 A1 | 11/2016 |
| WO | 2017/019634 A1 | 2/2017 |

OTHER PUBLICATIONS

Ughi, et al., "Automated tissue characterization of in vivo atherosclerotic plaques by intravascular optical coherence tomography images", Optical Society of America, Biomedical Optics Express, vol. 4, No. 7, Jul. 2013, pp. 1014-1030.

Fard, et al., "Optical coherence tomography—near infrared spectroscopy system and catheter for intravascular maging", Optics Express, vol. 21, No. 25, Dec. 2013, pp. 30849-30858.

Maehara, et al., "Assessment and Quantitation of Stent Results by Intracoronary Optical Coherence Tomography", Intervent. Cardiol. Clin., May 2015; 4(3), pp. 285-294.

Prati, et al., "Clinical Impact of OCT Findings During PCI: The CLI-OPCI II Study", JACC Cardiovascular Imaging, Nov. 2015, vol. 8, No. 11, pp. 1297-1305.

Ughi, et al., "Clinical Characterization of Coronary Atherosclerosis With Dual-Modality OCT and Near-Infrared Autofluorescence Imaging", Coronary OCT-NIRAF Imaging, American College of Cardiology Foundation, JACC Cardiovascular Imaging, Mar. 2016, vol. 9, No. 11, pp. 1304-1314, ISSN 1936-878X, 2016 https://www.researchgate.net/publication/297722095_Clinical_Characterization_of_Coronary_Atherosclerosis_With_Dual-Modality_OCT_and_Near-Infrared_Autofluorescence_Imaging.

Horsley, E., "Imaging for the Future; Intravascular Optical Coherence Tomography", Sep. 10, 2016; from https://www.slideshare.net/ErnestHorsley/coronary-optical-coherence-tomography-oct-angio-coregistration-acr-and-metal-stent-optimisation-mso-softwarefrom (42 pages).

St Jude Web Page "OPTIS Stent Optimization Software", last updated Feb. 10, 2017: https://www.sjmglobal.com/professionals/resources-and-reimbursement/technical-resources/vascular/intravascular-diagnostics-and-imaging/Intravascular-diagnostics-and-imaging-system-ffr-oct/optis-metallic-stent-optimization-software?halert=show&clset=92f57278-460e-4300-b7fe-89e52a04194f%3acadddb93-fcc4-47f2-8ceb-fd88f01ca17f (3 pages).

IntelliSpace Portal 8.0 Brochure http://www.biessemedica.it/images/virtuemart_product_sheet/soluzioni_it/IntelliSpace_Portal_8_brochure.pdf, obtained online on Feb. 2, 2018, at: http://www.biessemedica.it/images/virtuemart_product_sheet/soluzioni_it/IntelliSpace_Portal_8_brochure.pdf.

* cited by examiner

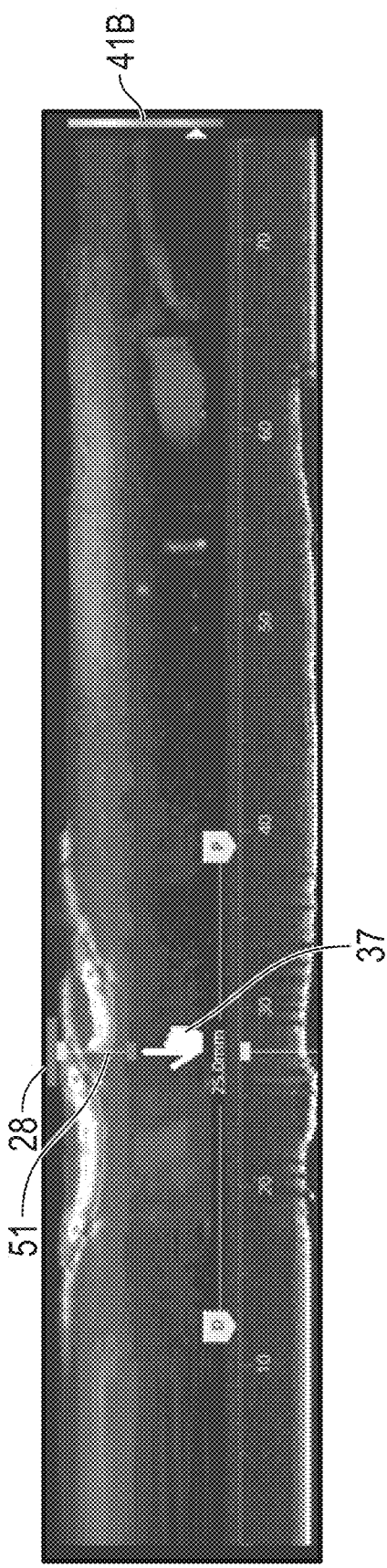
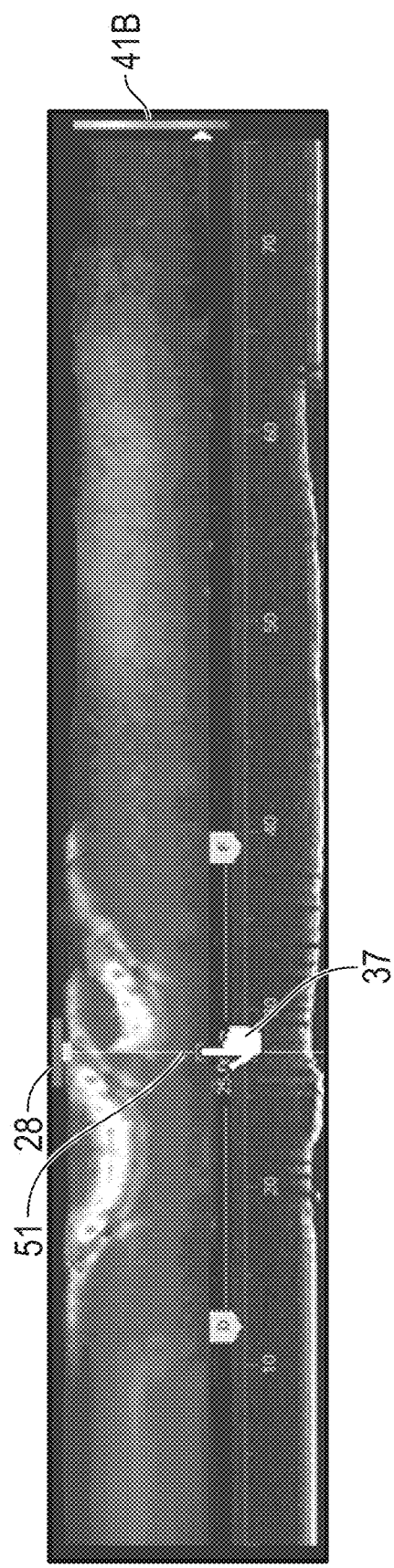
FIG. 8A
FIG. 8B

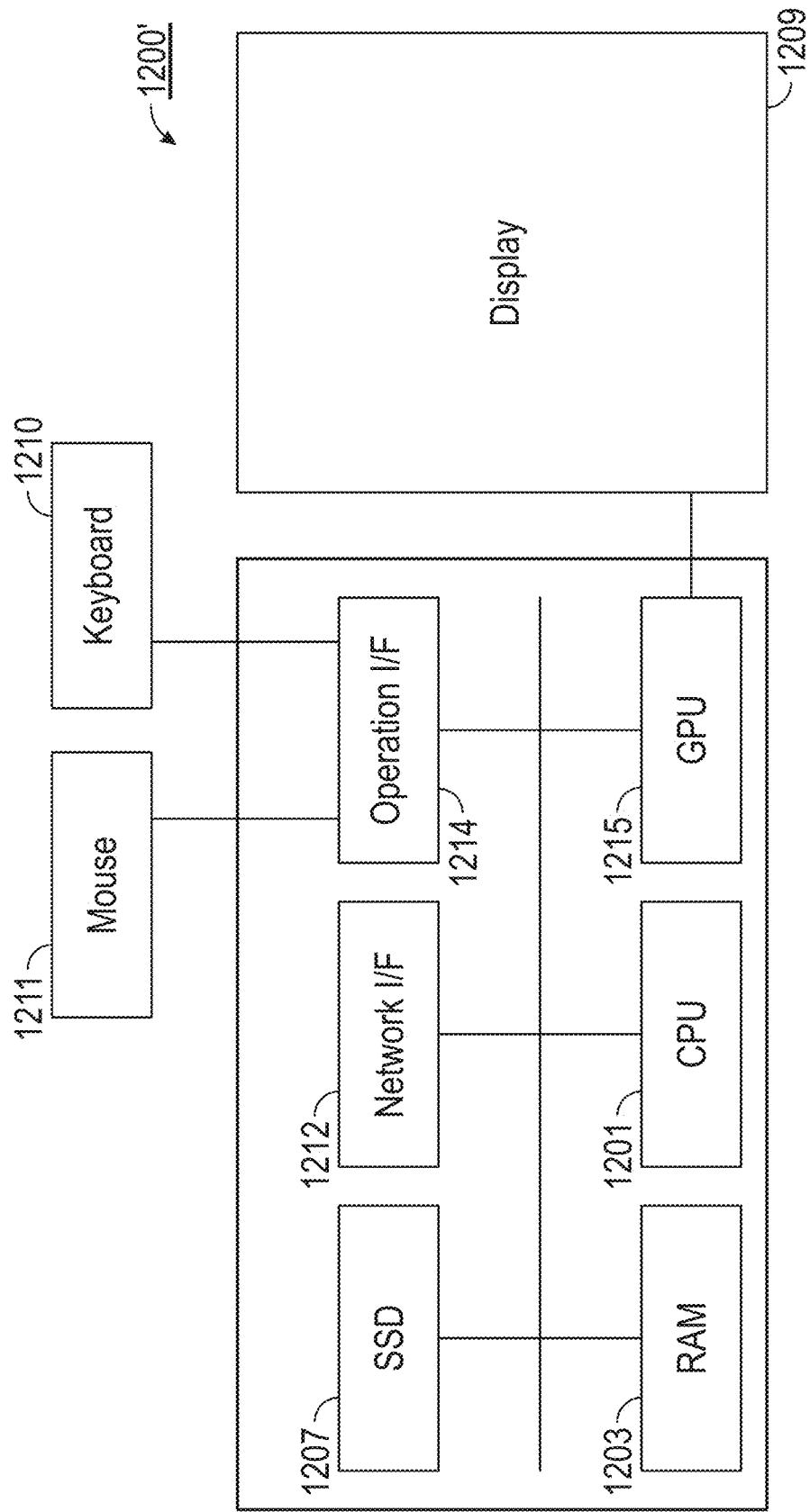

DEVICES, SYSTEMS, AND METHODS TO EMPHASIZE REGIONS OF INTEREST ACROSS MULTIPLE IMAGING MODALITIES

CROSS-REFERENCE TO RELATED APPLICATION(S)

This application relates, and claims priority, to U.S. Patent Application Ser. No. 62/666,252, filed May 3, 2018, the entire disclosure of which is incorporated by reference herein in its entirety.

FIELD OF THE INVENTION

This present disclosure generally relates to computer imaging and/or to the field of optical imaging, particularly to devices, systems, methods, and storage mediums for using multiple imaging modalities, such as, but not limited to, Optical Coherence Tomography (OCT), Multi-mode OCT (MMO-OCT), near-infrared fluorescence (NIRAF), etc. Examples of OCT applications include imaging, evaluating and diagnosing biological objects, such as, but not limited to, for gastro-intestinal, cardio and/or ophthalmic applications, and being obtained via one or more optical instruments, such as, but not limited to, one or more optical probes, one or more catheters, one or more endoscopes, one or more capsules, and one or more needles (e.g., a biopsy needle). One or more devices, systems, methods and storage mediums for characterizing, examining and/or diagnosing, and/or measuring viscosity of, a sample or object in application(s) using an apparatus or system that uses and/or controls multiple imaging modalities are discussed herein.

BACKGROUND OF THE INVENTION

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are.

During vascular diagnosis and intervention procedures, such as Percutaneous Coronary Intervention (PCI), users of optical coherence tomography (OCT) sometimes have difficulty understanding the tomography image in correlation with other modalities because of an overload of information, which causes confusion in image interpretation.

Accordingly, it would be desirable to provide at least one imaging or optical device, system, method, and storage medium for using, controlling, and/or emphasizing multiple imaging modalities, for example, by using an interface which provides a way to more fully comprehend the molecular structure of the vessel by providing an intuitive means to manipulate the vessel information is needed.

SUMMARY OF THE INVENTION

Accordingly, it is a broad object of the present disclosure to provide imaging (e.g., OCT, NIRAF, etc.) apparatuses, systems, methods and storage mediums for using and/or controlling multiple imaging modalities. It is also a broad object of the present disclosure to provide OCT devices, systems, methods and storage mediums using an interference optical system, such as an interferometer (e.g., SD-OCT, SS-OCT, etc.).

One or more embodiments provide at least one intuitive Graphical User Interface (GUI), method, device, apparatus, system, or storage medium to comprehend information, including, but not limited to, molecular structure of a vessel, and to provide an ability to manipulate the vessel information.

The present disclosure describes a means to allow OCT users to focus on the area of interest in all imaging modalities, such as, but not limited to, a tomography image, near-infrared fluorescence (NIRAF) information in carpet view, three-dimensional (3D) rendering of a coronary vessel in a half pipe display, lumen diameter display, longitudinal view, and angiography view. As described below, all of the displayed imaging modalities may be controlled by any one of several control bars which allow the user to change and update each display, synchronously, and to highlight NIRAF data when appropriate. This allows the users to get a full view of the structural vessel information using multi-modalities and also allow configurability of the function for more targeted focus.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

According to other aspects of the present disclosure, one or more additional devices, one or more systems, one or more methods and one or more storage mediums using OCT and/or other imaging modality technique(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 8A-8B show at least one embodiment example of a control bar before and after being adjusted, respectively, in accordance with one or more aspects of the present disclosure;

FIG. 18 shows a schematic diagram of another embodiment of a computer that may be used with one or more embodiments of an imaging apparatus or system or methods discussed herein in accordance with one or more aspects of the present disclosure.

DETAILED DESCRIPTION OF THE PRESENT INVENTION

One or more devices, systems, methods and storage mediums for characterizing tissue, or an object or sample, using multiple imaging techniques or modalities (such as, but not limited to, OCT, NIRAF, etc.) are disclosed herein. Several embodiments of the present disclosure, which may be carried out by the one or more embodiments of an apparatus, system, method and/or computer-readable storage medium of the present disclosure are described diagrammatically and visually in FIGS. 1 through 18.

Turning now to the details of the figures, imaging modalities may be displayed in one or more ways as discussed herein. One or more displays discussed herein may allow a user of the one or more displays to use, control and/or emphasize multiple imaging techniques or modalities, such as, but not limited to, OCT, NIRAF, etc., and may allow the user to use, control, and/or emphasize the multiple imaging techniques or modalities synchronously.

Figure 1:
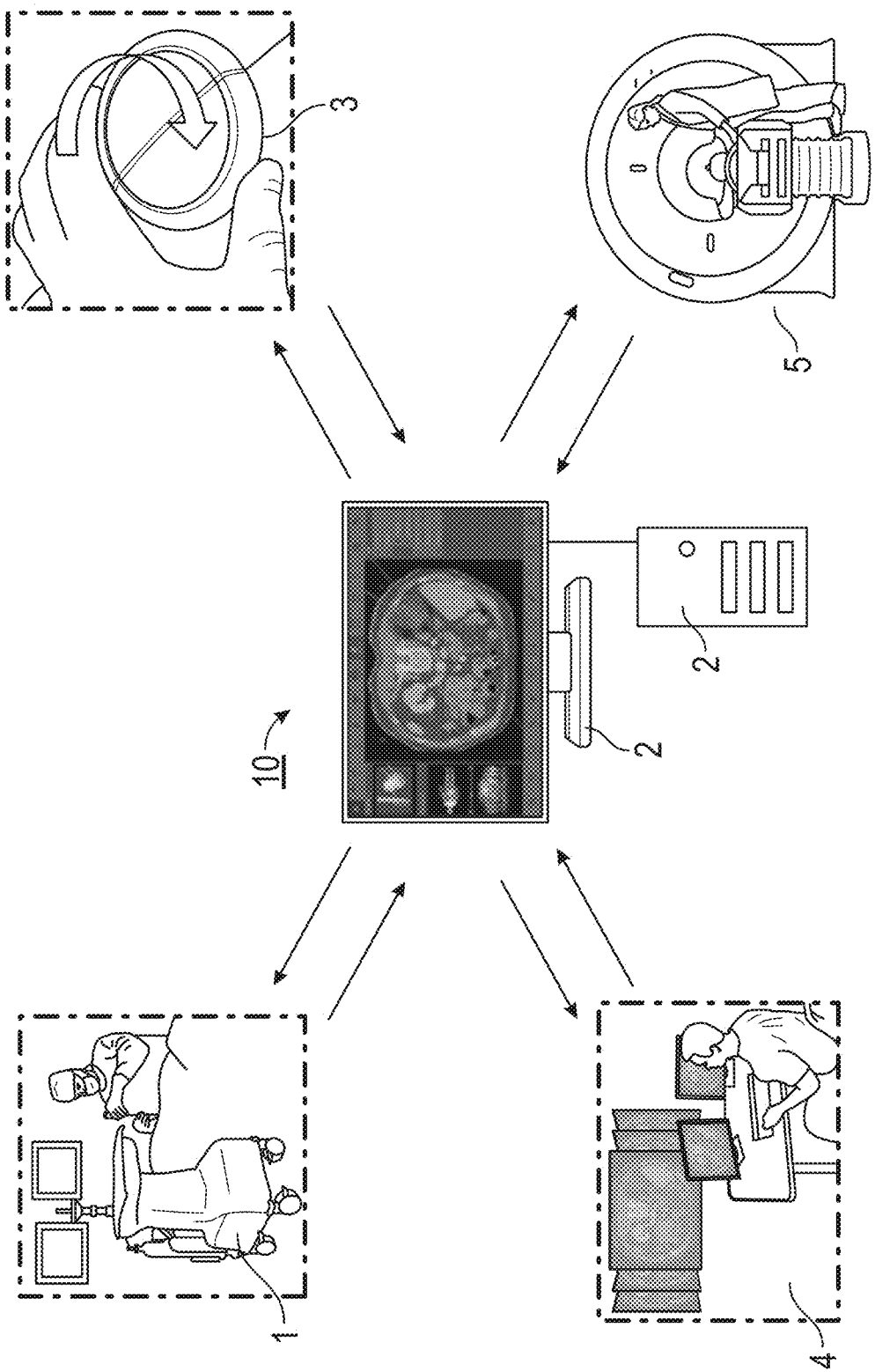
FIG. 1 is a schematic diagram showing at least one embodiment of a system that may be used for performing multiple imaging modality viewing and control in accordance with one or more aspects of the present disclosure.

As shown diagrammatically in FIG. 1, one or more embodiments for visualizing, emphasizing and/or controlling multiple imaging modalities of the present disclosure may be involved with one or more predetermined or desired procedures, such as, but not limited to, medical procedure planning and performance. For example, the system 2 may communicate with the image scanner 5 to request information for use in the medical procedure (e.g., ablation) planning and/or performance, such as, but not limited to, bed or slice positions, and the image scanner 5 may send the requested information along with the images to the system 2 once a clinician uses the image scanner 5 to obtain the information via scans of the patient. By way of another example, the system 2 may communicate and be used with a locator device 3 (such as an image-plane localizer that may be a patient-mount device and may be rotated as shown to help locate to a biological object, such as, but not limited to, a lesion or tumor, another predetermined part of an object, subject or sample, etc.) to obtain information from the patient when conducting the medical procedure planning and/or performance. The system 2 may further communicate with a PACS 4 to send and receive images of a patient to facilitate and aid in the medical procedure planning and/or performance. Once the plan is formed, a clinician may use the system 2 along with a medical procedure/imaging device 1 (e.g., an imaging device, an OCT device, an ablation device, etc.) to consult a medical procedure chart or plan to understand the shape and/or size of the targeted biological object to undergo the imaging and/or medical procedure. Each of the medical procedure/imaging device 1, the system 2, the locator device 3, the PACS 4 and the scanning device 5 may communicate in any way known to those skilled in the art, including, but not limited to, directly (via a communication network) or indirectly (via one or more of the other devices 1, 3 or 5; via one or more of the PACS 4 and the system 2; via clinician interaction; etc.).

Figure 2:
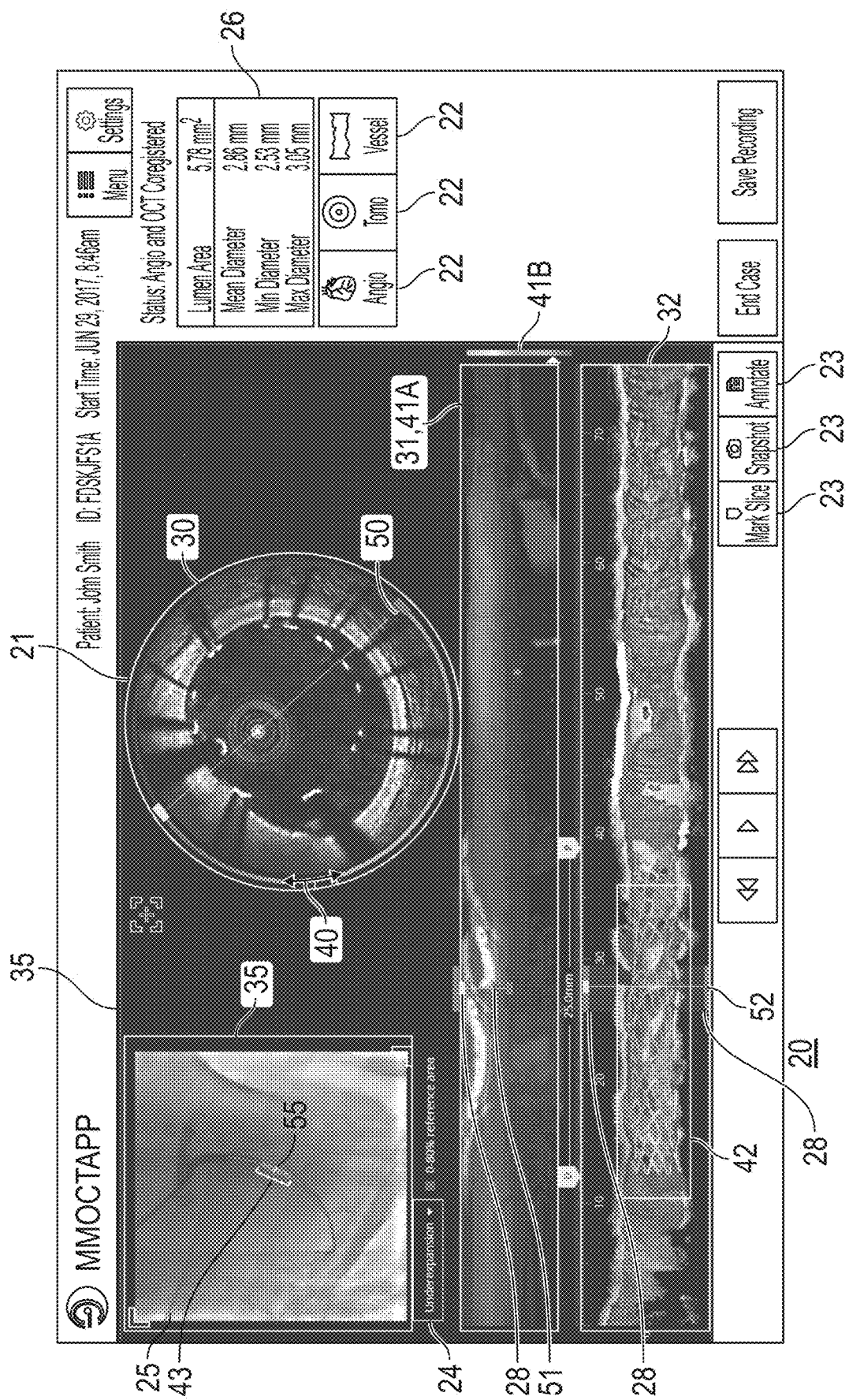
FIG. 2 is at least one embodiment example of a Graphical User Interface (GUI) that may be used for performing multiple imaging modality viewing and control in accordance with one or more aspects of the present disclosure.

FIG. 2 shows a multi-modality graphical user interface (GUI or UI) 20 that includes four (4) imaging modalities as a default display according to at least a first embodiment of the present disclosure. For example, Imaging Modality 1 (IM1) 30 shows an OCT image 21 with NIRAF data (NS1) 40 displayed in a full circle around the outer edge of the OCT image and a rotational control bar (CB1) 50, with two (2) handle bars and a circle in the center which is overlaid and merged with half of the NIRAF data angled at −45 degrees or approximately −45 degrees by default (with respect to a horizontal axis extending from left to right through IM1 30) in one or more embodiments. Any other discussion of a −45 degree angle in the present disclosure may likewise be modified or changed, or may be set to a different angle automatically or manually as discussed herein. In one or more other embodiments, the orientation angle may be any predetermined or angle desired by a user, for example, 90 degrees (or −90 degrees), 45 degrees, 40 degrees (or −40 degrees), 50 degrees or −50 degrees, or any other orientation within the 360 degree range. One or more embodiments may include feature options 22 (e.g., angio controls, tomo controls, vessel controls, etc.) where when a user highlights a mouse icon or pointer over one of these feature options 22, a drop down menu may appear with features or options related to the chosen feature option 22. For example, for the angio controls, one or more embodiments may provide an option(s) to view the NIRAF signal super-imposed on the angio image, and one or more embodiments may show a stent option to show an existing stent super-imposed on the angio image. By way of another example, for the tomo controls, an option(s) may be to show one or more of the following: the NIRAF signal, the stent, EEL (External Elastic Lamina, which may place an indicator (e.g., a dotted circle, a circle, a box, a geometric shape or other indicator, etc.) at a predetermined location in the image (e.g., in a center, a user selected location, at a location in relation to the tomo image (top right image shown in FIG. 2), etc.) and which may allow the user to adjust the location and save that data), at least one Lumen (Edge), at least one length (e.g., showing or drawing a line between two points), a rotational feature (e.g., a rotational bar). By way of a further example, for the vessel controls, one or more embodiments may provide an option(s) to see or view one or more of the following: a NIRAF Carpet View (see e.g., the view showing IM2, NS2A, NS2b, and CB2 in FIG. 2), a three-dimensional (3D) Half Pipe, a Lumen Profile, Raw Data, a Stent, and/or at least one Guidewire. In one or more embodiments, the features may be moved to other locations shown in the GUI, such as, but not limited to, amongst feature locations for features 22, 23, 24, any other location for a shown feature, etc. For example, in one or more embodiments, the EEL option may be a drop down option included in the option icon 23 discussed below.

As shown in FIG. 2, other options 23 may be included in the GUI, such as, but not limited to, a Mark Slice feature, a Snapshot feature, an Annotation feature, etc. The Snapshot feature operates to take a snapshot or image of the current view of the GUI. The Annotation feature operates to allow a user of the GUI to include a comment(s) or note(s) for the viewed image or images. The Mark Slice feature allows the user to set points in a pullback feed of slices that are of interest (i.e., to mark a desired slice or slices).

Another option, in one or more embodiments, is a setting or feature icon or drop down menu 24 that allows a user of the GUI to calculate one or more details of the image(s), such as, but not limited to, expansion/underexpansion (e.g., related to a reference area, of a stent, etc.), malapposition (e.g., of a stent, of a medical implant, etc.), etc. Information may be displayed to the right of menu 24, such as, but not limited to, a percentage value of the reference area (e.g., "0-80% reference area" which indicates underexpansion exists in one or more embodiments and ma may be associated with a red box (or a box of a predetermined color) near or to the left of that information; "80-90% reference area" which may indicate that an issue may or may not exist (e.g., the underexpansion may fall within an acceptable range) related to underexpansion and may be associated with a yellow box (or a box of a predetermined color) near or to the left of that information, "90-100% reference area" which may indicate that an issue may not exist related to underexpansion and may be associated with a green box (or a box of a predetermined color) near or to the left of that information; etc.). Any colored box may be set at a predetermined location other than as shown in FIG. 2 as desired in one or more embodiments. Such information and indicators may be used for apposition/malapposition in one or more embodiments. Additionally or alternatively, apposition/malapposition may be indicated with different predetermined ranges, such as, but not limited to, for example, greater than 300 microns (in other words, 300 microns or greater) may be used as the range for the red region or a region that needs or may need correction or action (e.g., a high risk region); between 200-300 microns may be used for the yellow region or a region that may need correction or action or to be watched closely or a region that is in an acceptable range to take no action or make no correction (e.g., a region between high and low risk, an acceptable region, etc.); less than 200 microns may be used for the green region or a region that has no issue detected and/or may require no action (e.g., a low risk region); etc. In one or more embodiments, different values or ranges may be assigned to the limits or ranges for the red or high risk region, the yellow or middle region and/or the green or acceptable region, for instance. The subject ranges may be decided by the apparatus, GUI, system, method, or storage medium automatically or may be selected by a user (e.g., a physician) manually. Depending on the application and use of the one or more embodiments of the present disclosure, such values may change accordingly. Other ranges may be designated for the high/low risk and/or acceptable or attention needed regions depending on the needs of a user and the medical procedure to be performed. Based on the data and associated warning or information displayed related to expansion/underexpansion and/or the apposition/malapposition, the GUI operates to indicate to a user of the GUI how to respond to that information (e.g., expansion/underexpansion and/or apposition/malapposition falls within an acceptable range such that no action may be needed; expansion/underexpansion and/or apposition/malapposition falls outside of an acceptable range such that action may be needed; expansion/underexpansion and/or apposition/malapposition falls in a range that requires correction or correction may be suggested; etc.). Any of the subject ranges (or any other range or ranges discussed in the present disclosure) may be selected manually or automatically as aforementioned. Such examples allow a user of the GUI to identify potential issues identified by the data in the one or more images, and may make appropriate decisions and create a plan accordingly.

Such information and other features discussed herein may be applied to other applications, such as, but not limited to, co-registration, other modalities, etc. Indeed, the useful applications of the features of the present disclosure are not limited to the discussed modalities, images, or medical procedures. Additionally, depending on the involved modalities, images, or medical procedures, one or more control bars (e.g., control bar1 50) may be contoured, curved, or have any other configuration desired or set by a user. For example, in an embodiment using a touch screen as discussed herein, a user may define or create the size and shape of a control bar based on a user moving a pointer, a finger, a stylus, another tool, etc. on the touch screen (or alternatively by moving a mouse or other input tool or device regardless of whether a touch screen is used or not).

One or more methods or algorithms for calculating expansion/underexpansion or apposition/malapposition may be used in one or more embodiments of the instant application, including, but not limited to, the expansion/underexpansion and apposition/malapposition methods or algorithms discussed in U.S. Pat. Pub. Nos. 2019/0102906 and 2019/0099080, which publications are incorporated by reference herein in their entireties. For example, in one or more embodiments for evaluating expansion/underexpansion, a method may be performed to remove inappropriate OCT image frames from the OCT image from further image processing. The result of lumen detection may be checked for each OCT image frame. If the lumen is not detected or if the detected lumen is affected by any artifact, the OCT image frame may be removed. A first OCT image frame is selected from the OCT image in a first step. After selecting the first OCT image frame, it may be determined whether a lumen is detected in the selected OCT image frame. If it is determined that no lumen has been detected in the OCT image frame, then the OCT image frame may be removed from further image processing and the process continues. Alternatively, if the lumen is detected in the frame, then a further determination of whether the detected lumen is affected by any artifact may be performed. If the detected lumen is affected by an artifact, then the OCT image frame may be removed from further processing and the process proceeds. If the detected lumen is not affected by any artifact, then it may be determined if the selected OCT image frame is the last OCT image frame from the OCT image. If the selected frame is not the last frame in the OCT image, then the next OCT image frame from the OCT image may be selected and the process returns to the lumen detection on the frame step. If the selected OCT image frame is the last OCT image frame, then the process proceeds. After removing the inappropriate OCT image frames, all the OCT image frames in which stent-struts are detected may be selected (Group $G_s'$). It may that the entire range of the stent region in the OCT image is going to be evaluated for stent expansion in one or more embodiments, but in another embodiment in this step a user may select one or more (first) ranges for evaluating stent expansion, from the stent region where the stent is implanted and the stent-struts are detected. Whether the user selects the first range as the entire range of the stent region or as a partial range of the entire stent region may depend upon system requirements or user needs. In one embodiment, the user may use a mouse device or touch screen device to designate one or more (first) ranges in the stent region, and a processor or CPU (e.g., the computer or processor 1200, 1200', 2, etc. and/or any other processor discussed herein) may determine the first range for the stent expansion evaluation. This allows for designation of one or more positions. Subsequently, a reference OCT image frame based on the confirmed stented region may be selected. If the calculated stent length is equal to or within a predetermined threshold to the actual stent length, the OCT image frame at a position representing the distal end and the OCT image frame at a position representing the proximal end of the stented segment may be selected as reference frames. If the calculated stent length is not equal to the actual stent length and not within a predetermined threshold, the reference frames may be selected based on either the calculated stent length or the actual stent length. When the calculated stent length is selected for reference frame selection, the OCT image frame at a position representing the distal end and the OCT image frame at a position representing the proximal end of the stented segment may be selected as reference frames. Then, a reference OCT image frame may be selected based on the confirmed stented region. The reference area in the selected reference frame may be evaluated. Then, the first OCT image frame from the OCT image frames in which stent-struts are detected may be selected. Then the stent area is measured for the first OCT image frame. After measuring the stent area of the first OCT image frame, stent expansion may be evaluated by comparing the measured stent area and the reference area. The stent expansion value and an indicator for the corresponding stent expansion level may be saved with the first OCT image frame. After the stent expansion value is saved, it is determined whether the selected OCT image frame is the last frame. If the selected OCT image frame is not the last frame, then the next OCT image frame is selected and the process returns to the aforementioned measuring stent area step. In this example, because the selected OCT image frame is the first OCT image frame, the next frame would be the second OCT image frame from the group of all the OCT image frames in which stent-struts were detected. After selecting the next OCT image frame the process returns to the measure stent area step to measure the stent area for the next OCT image frame. Alternatively, if it is determined that the selected OCT image frame is the last frame, then the process for evaluating stent expansion is completed for the acquired OCT image. According to this workflow, every OCT image frame in which stent-struts are detected and not affected by artifact may be processed to obtain a stent expansion value based on the stent area associated with a selected OCT image frame and a reference area. In one or more embodiments, the reference area remains the same for each OCT image frame from the OCT image frames in which stent-struts are detected and not affected by artifact. By way of another example, in one or more embodiments for evaluating apposition/malapposition, a method may be performed to remove inappropriate OCT images as aforementioned. The result of lumen detection may be checked for each OCT image frame. If the lumen is not detected or if the detected lumen is affected by any artifact, the OCT image frame may be removed. A first OCT image frame is selected from the OCT image in a first step. After selecting the first OCT image frame, it may be determined whether a lumen is detected in the selected OCT image frame. If it is determined that no lumen has been detected in the OCT image frame, then the OCT image frame may be removed from further image processing and the process continues. Alternatively, if the lumen is detected in the frame, then a further determination of whether the detected lumen is affected by any artifact may be performed. If the detected lumen is affected by an artifact, then the OCT image frame may be removed from further processing and the process proceeds. If the detected lumen is not affected by any artifact, then it may be determined if the selected OCT image frame is the last OCT image frame from the OCT image. If the selected frame is not the last frame in the OCT image, then the next OCT image frame from the OCT image may be selected and the process returns to the lumen detection on the frame step. If the selected OCT image frame is the last OCT image frame, then the process proceeds. After removing the inappropriate OCT image frames, all the OCT image frames in which stent-struts are detected may be selected (Group $G_s'$). Then, a first OCT image frame from the selected OCT image frames in which stent-struts are detected may be selected. Subsequently, for the selected first OCT image frame, the distance between the lumen edge and stent-strut detected in first OCT image frame may be measured. Stent apposition may be evaluated. The stent apposition may be evaluated by comparing the measured distance between the lumen edge and stent-strut to the stent-strut width that is obtained from the stent information. The stent apposition value and an indicator for stent apposition level may be saved for the corresponding OCT image frame. Then, it may be determined whether the selected OCT image frame is the last OCT image frame, if the selected frame is the last frame, then the process ends. In this example the selected OCT image frame is the first OCT image frame, so a second OCT image frame is selected and the process returns to the aforementioned measure distance step. The process repeats until each OCT image frame selected is evaluated and a stent apposition value is obtained.

The angiography (or angio) image 25 may be displayed on the top left of the GUI as shown in FIG. 2. Imaging Modality (IM6) shows the Angiography image 25 with the NIRAF data (NS6) displayed along the vessel on IM6. The control bar (CB6) is a bar that appears horizontally along the vessel of IM6.

As shown in FIG. 2, the GUI may display one or more values 26 (e.g., lumen area, mean diameter, min. diameter, max. diameter, etc.). Such information may be used to determine or decide how to plan or proceed with a procedure, e.g., what stent size to use when the procedure relates to expansion/underexpansion or apposition/malapposition.

As aforementioned, evaluating underexpansion/expansion and/or apposition/malapposition are examples of some of the applications of one or more embodiments of the present disclosure. One or more embodiments of the present disclosure may involve one or more additional or alternative applications, such as, but not limited to, determining whether plaque tissue, or a buildup of calcium, requires further attention. Another application example may involve determining whether a rotor blade needs to be fixed or not. Another application example may involve identifying or determining diagnosis information, determining whether medical attention is needed or not, identifying a region of choice or interest, etc. An indicator may be used to show or indicate one or more of such applications, such as, but not limited to, the bands (e.g., a red band or bands) 28 as shown on the top and bottom (or on both ends) of control bar 52 in the bottom of FIG. 2, the band 28 on the top of control bar 51 in the middle of FIG. 2, the band 28 located above the pointer 37 in FIG. 4, the bars shown in FIGS. 5A-5B, etc.

Figure 3:
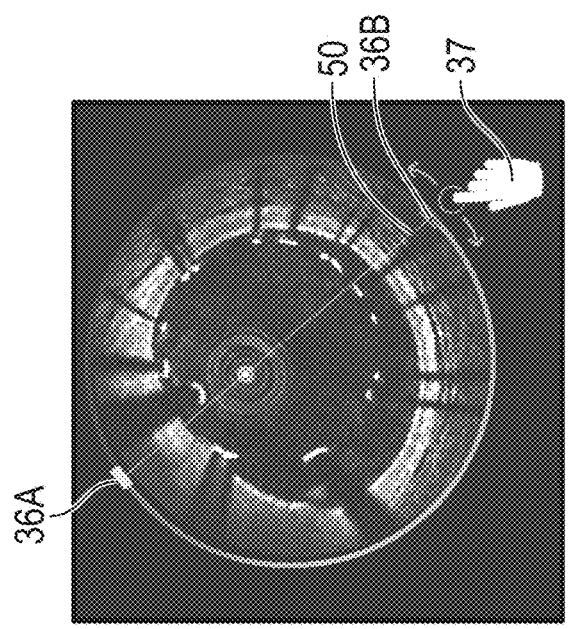
FIG. 3 is a partial view of an image having a control bar shown by at least one embodiment example of a GUI that may be used for performing multiple imaging modality viewing and control in accordance with one or more aspects of the present disclosure.

One or more embodiments of the present disclosure may include taking multiple views (e.g., OCT image, ring view, tomo view, anatomical view, etc.), and one or more embodiments may highlight or emphasize NIRAF. As shown in FIG. 3, the control bar (CB1) 50 may be moved bi-directionally, in a circular rotation. The two handles 36A, 36B are endpoints that may bound the color extremes of the NIRAF data in or more embodiments. In one or more embodiments, the two handles 36A, 36B may indicate a corresponding cut or area displayed in the 3D view.

Figure 4:
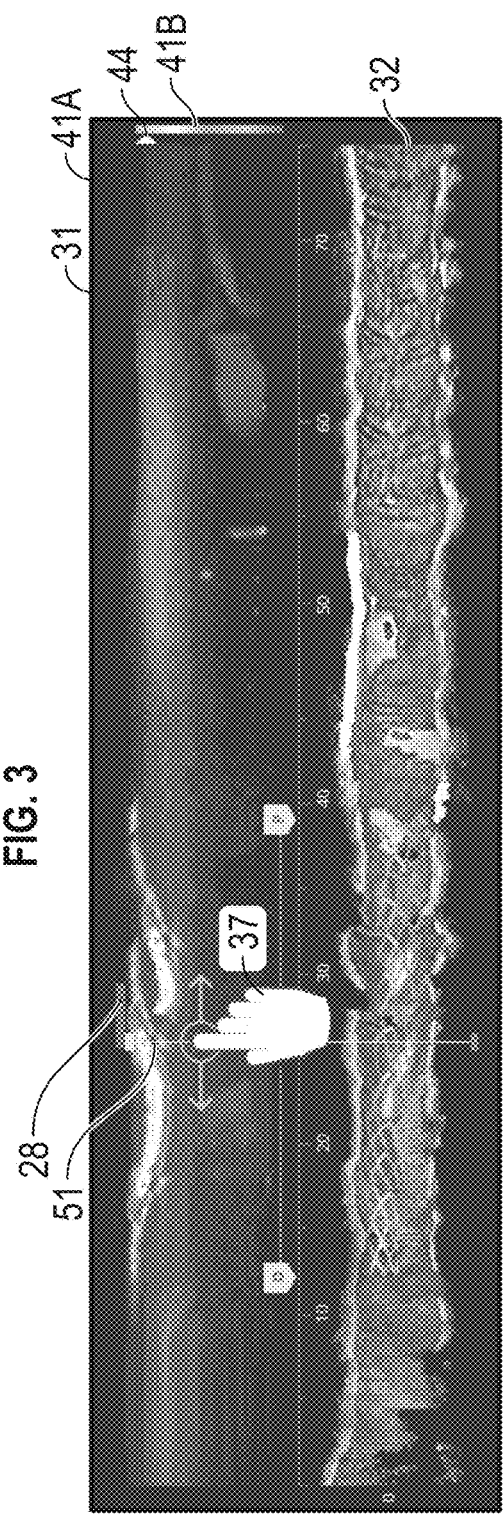
FIG. 4 is a partial view of an image having a control bar shown by at least one embodiment example of a GUI that may be used for performing multiple imaging modality viewing and control in accordance with one or more aspects of the present disclosure.

In one or more embodiments, Imaging Modality 2 (IM2) 31 shows NIRAF data (NS2A) 41A displayed in a carpet view (best seen in FIG. 2). The control bar (CB2) 51, with two handle bars, is displayed on half of the carpet view, that matches the half of NS1 40 around IM1 30. The control bar CB2 51 may be moved bi-directionally in a horizontal movement as illustrated in FIG. 4. The NIRAF signal gauge (NS2B) 41B highlights the greatest NIRAF signal intensity using an arrow 44 (best seen in FIG. 4), matching the highlighted half of the NS1 40 around IM1 30 (as shown in FIG. 2).

Figure 5A:
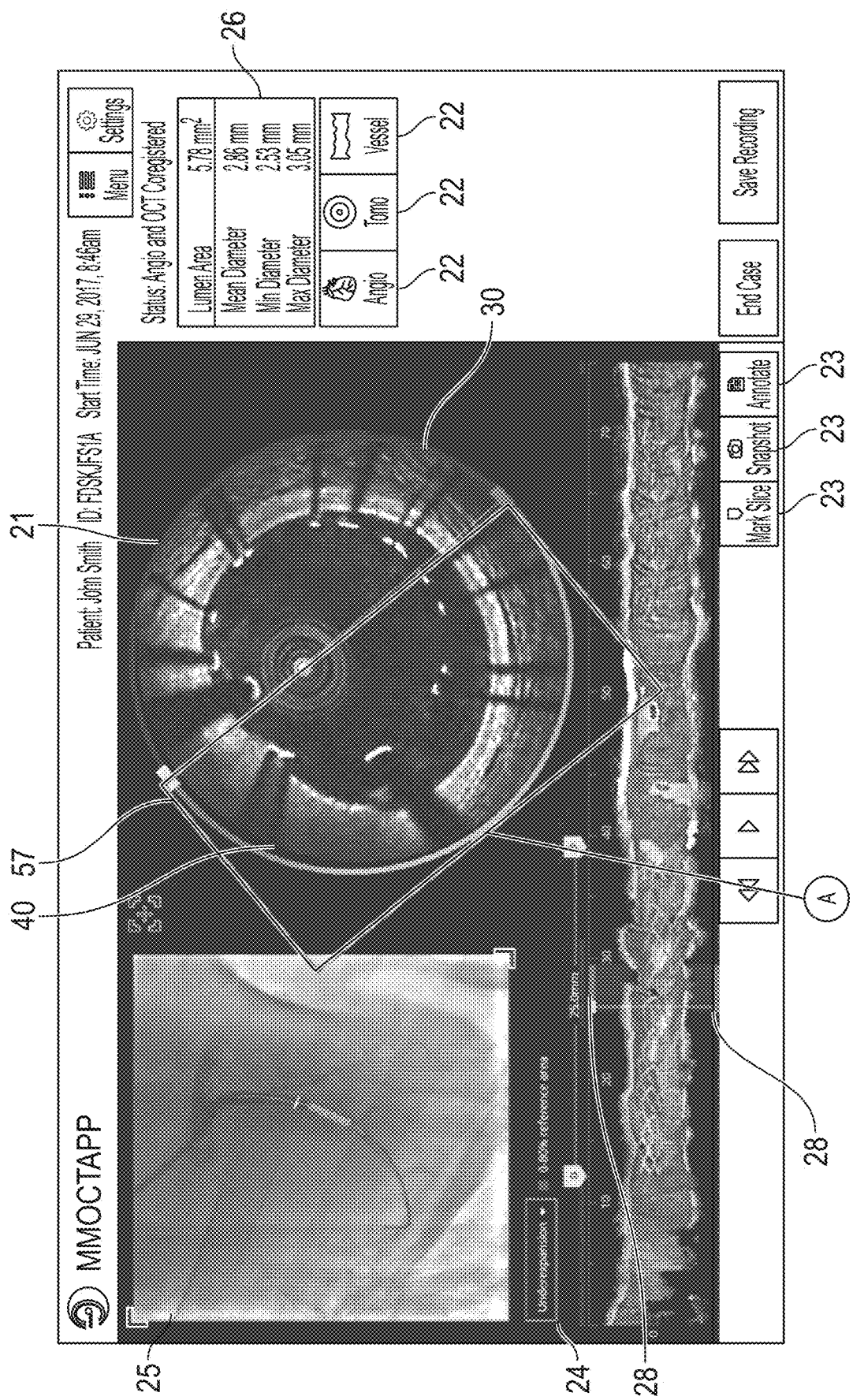
FIGS. 5A-5B are image examples of at least one embodiment of a GUI that may be used for performing multiple imaging modality viewing and control that shows a correlation between a tomo view and a half pipe vessel view in accordance with one or more aspects of the present disclosure.
Figure 5B:
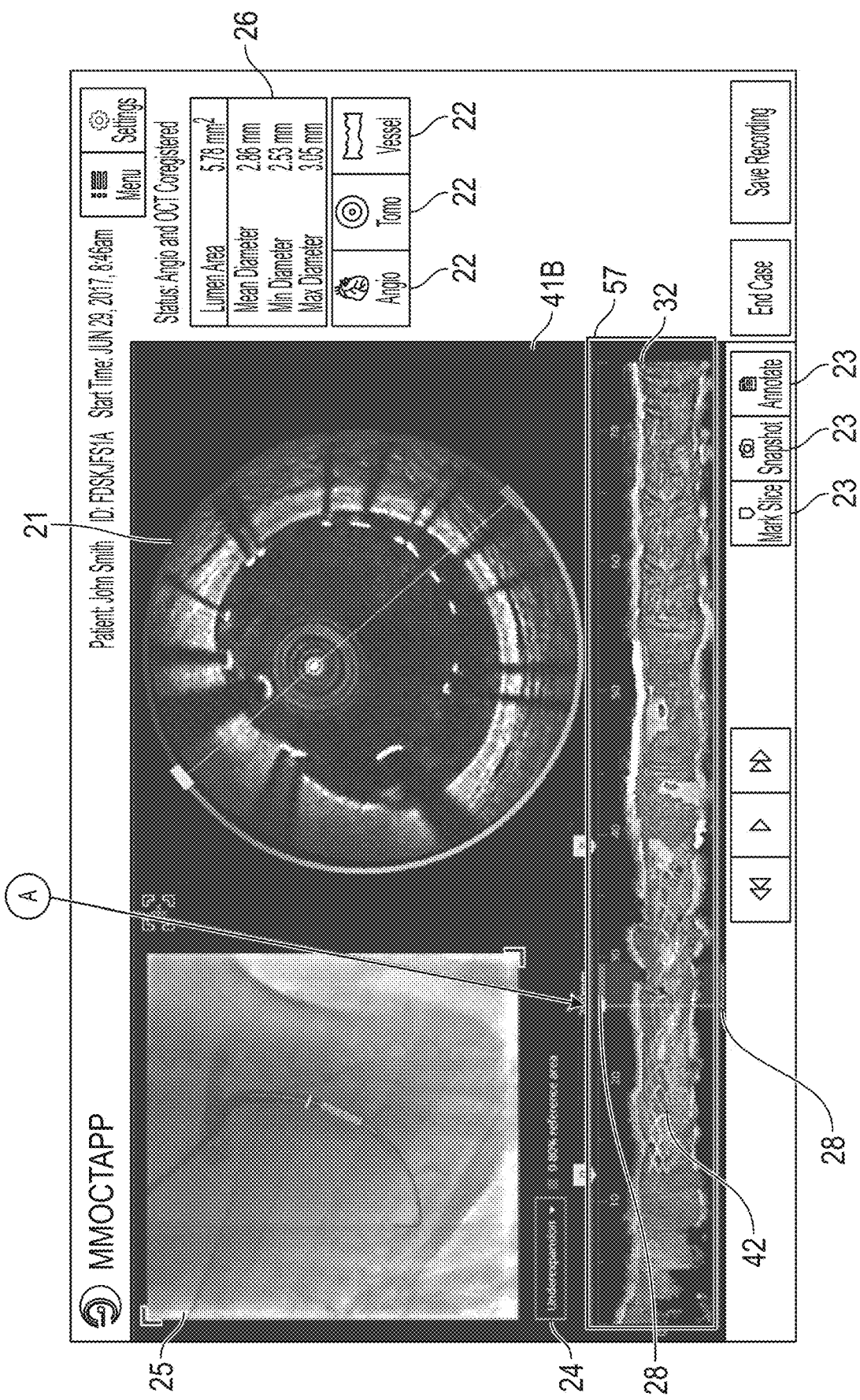

Imaging Modality 3 (IM3) 32 (as shown, for example, on the bottom of FIG. 2, as best shown in FIG. 4, etc.) shows a three-dimensional (3D) half pipe vessel view matching the highlighted half of the NS1 40 around IM1 30, and the NIRAF data (NS3) 42 displayed on the inner wall of IM3 32. The control bar (CB3) 52, with two handle bars, is displayed on IM3 32, matching the half of NS1 40 around IM1 30. FIGS. 5A-5B illustrate these features and/or correlations by use of the boxes 57 (showing a line connecting both box 57 in FIG. 5A to the box 57 in FIG. 5B as a visual representation of these features and/or correlations). The 3D half pipe of FIG. 4, for example, may be used in one or more embodiments for one or more of the applications discussed herein, including, but not limited to, confirming whether an additional corrective step or action is needed or confirming whether an issue has been handled successfully or completely. In at least one embodiment, the 3D half pipe rendering may be of an L view (or any predetermined view), and data may be taken from the NIRAF Carpet View (see aforementioned examples of a carpet view), and such data may be superimposed on the 3D half pipe (see e.g., FIGS. 8A-8B further discussed below). Such data may also be shown in any geometric shape. For example, the 3D rendering may be a shape other than a half pipe shape. If it is determined that a corrective or additional step is needed, then that step may be taken. For example, in the situation of underexpansion/expansion, a balloon may be inserted and inflated to expand a stent as needed or desired. After the corrective step or action is taken, a new 3D rendering (e.g., a 3D half pipe view) may be obtained or re-imaged, and it may then be determined if the issue has been addressed or additional step(s) or action(s) is/are needed.

As best seen in FIG. 2, Imaging Modality (IM6) 35 shows the Angiography image with the NIRAF data (NS6) 43 displayed along the vessel on IM6 35. The control bar (CB6) 55 is a bar that appears horizontally along the vessel of IM6 35.

Figure 6:
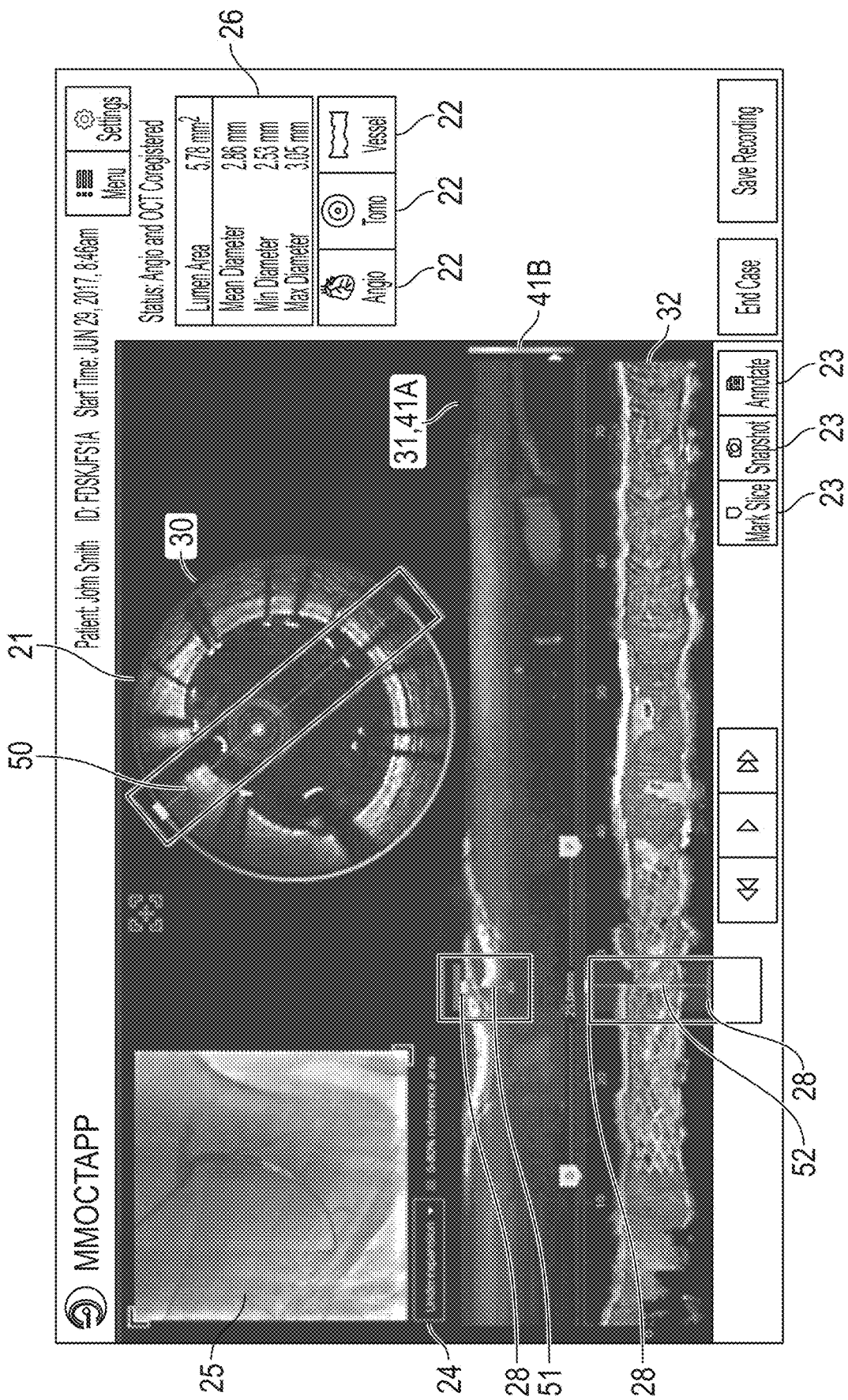
FIG. 6 shows at least one embodiment example of a GUI with positions of several control bars that may be used for performing multiple imaging modality viewing and control in accordance with one or more aspects of the present disclosure.

FIG. 6 shows control bars CB1 50, CB2 51, and CB3 52 on the OCT image 21, NIRAF data 41A displayed as a carpet view (see e.g., IM2 31), and reconstructed 3D, half pipe vessel view (see e.g., IM3 32), respectively. These displays are synchronized in a single image instance in each modality. Control bar CB1 50 is positioned to show half of the tomo (IM1) 30, highlighting half of the NIRAF data 41A. Control bar CB2 51 is positioned at the same image instance as IM1 30, highlighting half of the NIRAF data 41A splayed out in IM2 32, and control bar CB3 52 is positioned at the same image instance as IM1 30 and IM2 31, highlighting half of the 3D rendered vessel with the NIRAF data overlaid in IM3 32.

When one of the control bars CB1 50, CB2 51, CB3 52 is moved bi-directionally, all the other imaging modalities will update the corresponding displays according to a specific moment in time selected by the user. The data may be primarily focused and controlled on the display IM1 30 by using the control bar CB1 50 in one or more embodiments. As described above, the control bar CB1 50 may be moved bi-directionally so as to rotate in a circular motion around the OCT image 21. In one or more other embodiments, the data may be controlled and changed by using one of the other control bars CB2 51, CB3 52.

Figure 7:
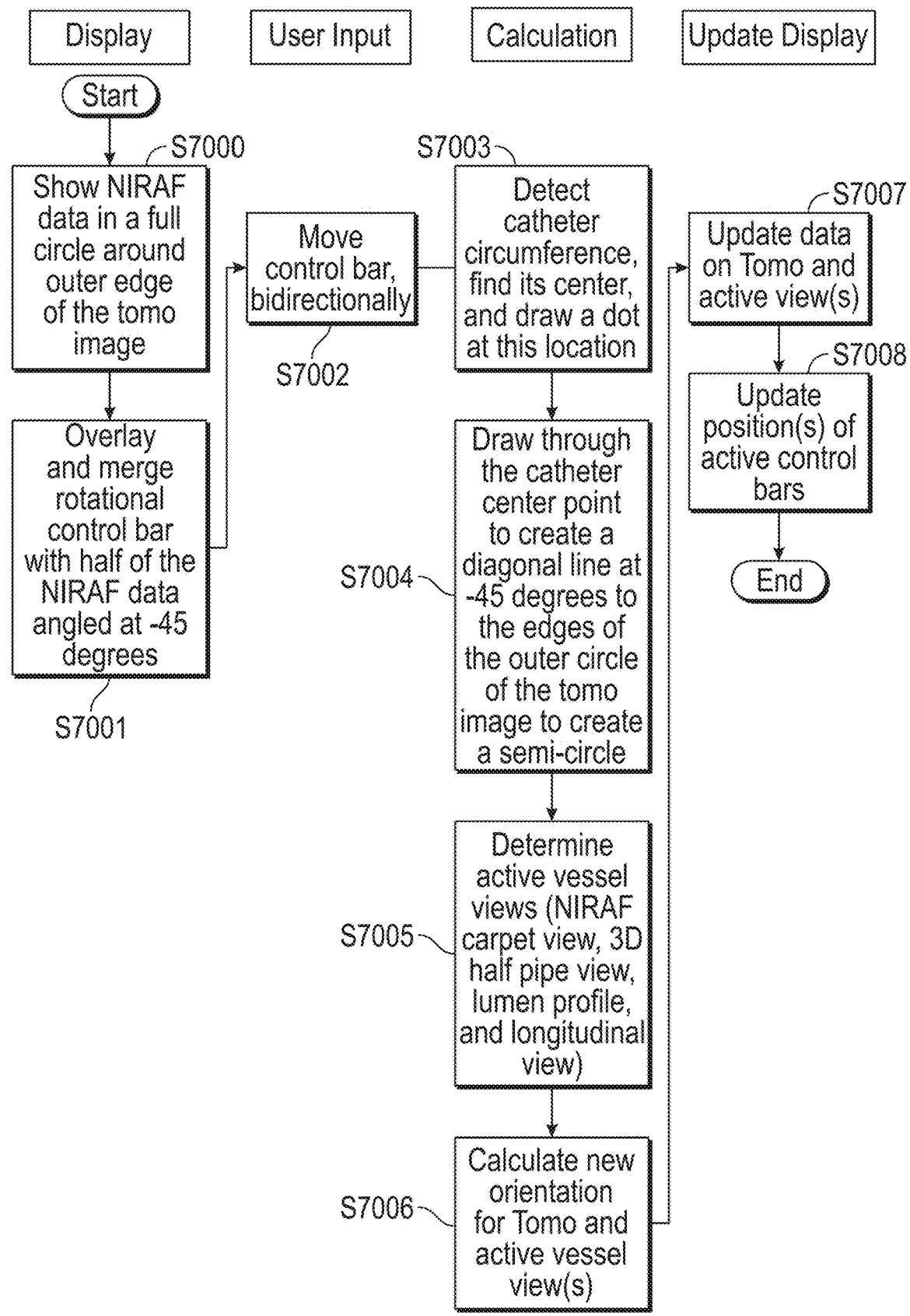
FIG. 7 is a flow diagram showing a method of performing control over multiple imaging modalities when input is received from a control bar in accordance with one or more aspects of the present disclosure.
Figure 9:
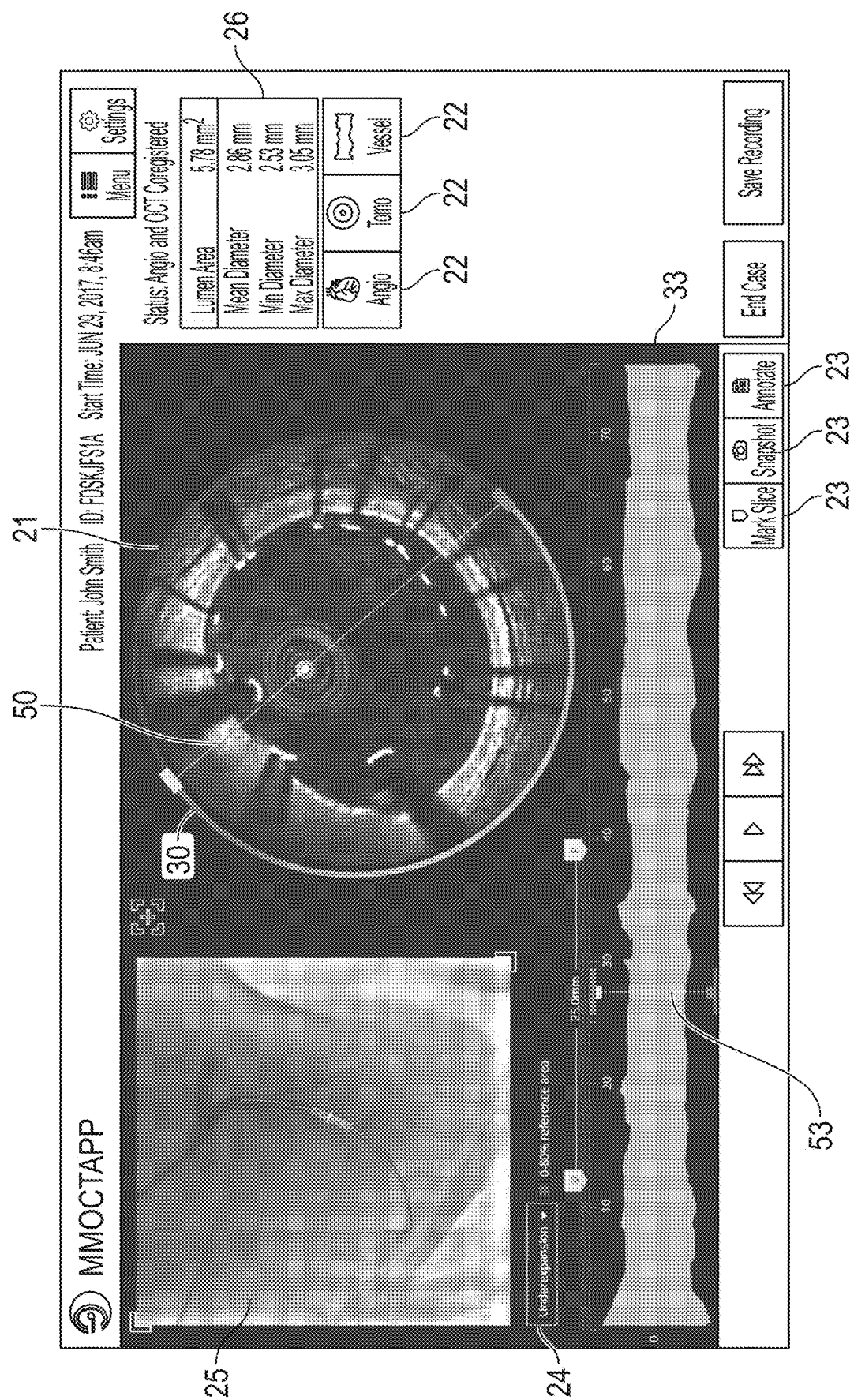
FIG. 9 shows at least one embodiment example of a GUI using an imaging modality which shows a lumen diameter of the vessel view in accordance with one or more aspects of the present disclosure.

FIG. 7 illustrates steps that may be performed when a control bar is manipulated, such as the control bar CB1 50 is manipulated on IM1 30, or an input is received from a control bar, such as the control bar CB1 50. Step S7000 as shown in FIG. 7 includes showing NIRAF data in a full circle around an outer edge of a tomo image. Step S7001 may include overlaying and merging a rotational control bar with half of the NIRAF data at a predetermined or selected angle (e.g., at −45 degrees). Step S7002 may involve moving a control bar (e.g., CB1 50, CB2 51, CB3 53, etc.), bi-directionally. Step S7003 may involve, on a selected IM, such as IM1 30, for example, a catheter circumference may be detected, a center of the circumference of the catheter may be found, and a dot may be drawn or disposed at this location. Step S7004, in one or more embodiments, may involve drawing through the catheter center point to create a diagonal line at −45 degrees to the edges of the outer circle of the OCT image 21 to create a semi-circle. The arc may represent half of the longitudinal view as illustrated, for example, in FIGS. 5A-5B. Step S7005 may involve determining active vessel views (e.g., NIRAF carpet view, 3D half pipe view, lumen profile, longitudinal view, etc.). Step S7006 may involve calculating a new orientation for a Tomo and active vessel view(s). Step S7007 may involve updating data on the Tomo and active view(s). Step S7008 may involve updating position(s) of active control bars.

One or more additional embodiments may include or involve the following steps 1 through 5:

Step 1: On IM1 30, detect the catheter circumference, find its center, and draw a dot at this location.

Step 2: Draw through the catheter center point to create a diagonal line at −45 degrees to the edges of the outer circle of the OCT image 21 to create a semi-circle. The arc represents half of the longitudinal view as illustrated in FIGS. 5A-5B.

Step 3: Determine active imaging modalities (e.g., IM1 30, IM2 31, IM3 32, and IM6 35).

Step 4: Calculate new orientation/position of control bars (e.g., CB1 50, CB2 51, CB3 52, and CB6 55) and active imaging modalities (e.g., IM1 30, IM2 31, IM3 32, and IM6 35).

Step 5: When calculations are complete, an updated display may be comprised of one or more of the following: (1) The positions of the control bars (e.g., CB1 50, CB2 51, CB3 52, and CB6 55) may be updated within each imaging modality; (2) The displays of NIRAF data (NS2A 41A, NS3 42, and NS6 43) may be updated; (3) Display IM2 31 may scroll vertically and update the display of NIRAF data (e.g., NS2A 41A, NS2B 41B, NS3 42, NS6 43, etc.); (4) Display IM3 32 may scroll vertically and update the 3D half pipe vessel view with NIRAF data overlaid on the vessel (see e.g., IM3 32); and (5) The NIRAF signal gauge (NS2B 41B) may reposition the arrow 44 to highlight the greatest NIRAF signal intensity matching to a highlighted half of a NIRAF ring (see e.g., as shown in FIGS. 3 and 4 as discussed above).

Alternatively, if the control bar CB2 51 changes position on IM2 31 by being moved bi-directionally, i.e., dragged horizontally (left and right) on the NIRAF carpet view as illustrated in FIG. 4, the same or similar calculations may be performed as described above.

If, instead of being moved horizontally, the control bar CB2 51 has one of its handle bars pulled vertically downward on IM2 31, the control bar CB1 50 on IM1 30 may become greater than 180 degrees. (See, for example, FIGS. 8A-8B). FIG. 8A shows an embodiment example of the control bar CB2 51 before a bottom handle of CB2 51 is pulled downward, and FIG. 8B shows an example of the control bar CB2 51 after the bottom handle of CB2 51 is pulled downward. In one or more embodiments, one or more of the subject control bars may have a different size or shape (e.g., contour, curve, etc.) as desired.

One or more alternative embodiments may have the same or similar default display, user input, calculations, and updated display from the aforementioned embodiments (see e.g., at least FIGS. 2-8B) pertaining to IM2 31, IM3 32, and IM6 35, but the control bar CB1 50 may not appear on IM1 30 in the one or more alternative embodiments.

Figure 11:
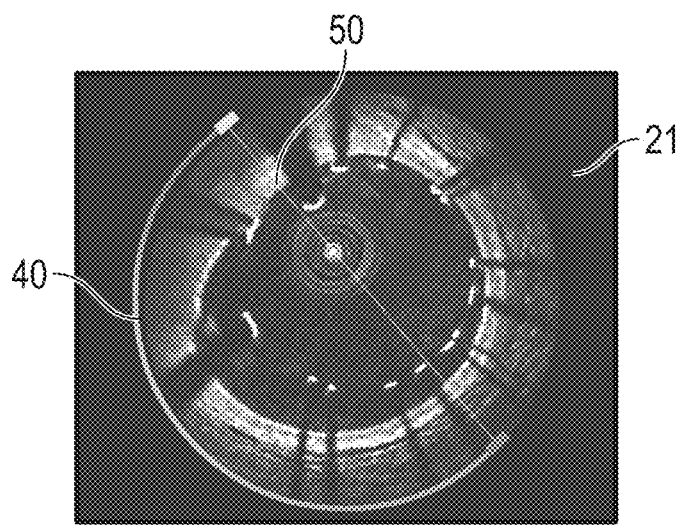
FIGS. 11-13 show partial views of respective alternative embodiments for images being displayed be one or more GUI's in accordance with one or more aspects of the present disclosure.

One or more further alternative embodiments may have the same or similar default display, user input, calculations, and updated display from the aforementioned embodiments, except NS1 40 may show a semi-circle of NIRAF data (as best seen in FIG. 11) instead of a full circle of NIRAF data (as shown, for example, in FIG. 12) around the OCT image 21.

Yet one or more further alternative embodiments may have the same or similar default display, user input, calculations, and updated display from the aforementioned embodiments (see e.g., at least FIGS. 2-8B) pertaining to IM1 30 and IM6 35, and shows Imaging Modality 4 (IM4) 33 (best seen in FIG. 9) which shows the lumen diameter of the vessel view, instead of IM2 31 and IM3 32. Here, control bars CB1 50 and CB4 53 are shown on the OCT image 21 and lumen profile (see e.g., IM4 33), respectively, and the displays are synchronized in a single image instance in each modality. (See FIG. 9). CB1 50 may be positioned to show half of the tomo (IM1 30) view highlighting half of the NIRAF data, and CB4 53 may be positioned at the same image instance as IM1 30, highlighting the lumen diameter.

Figure 10:
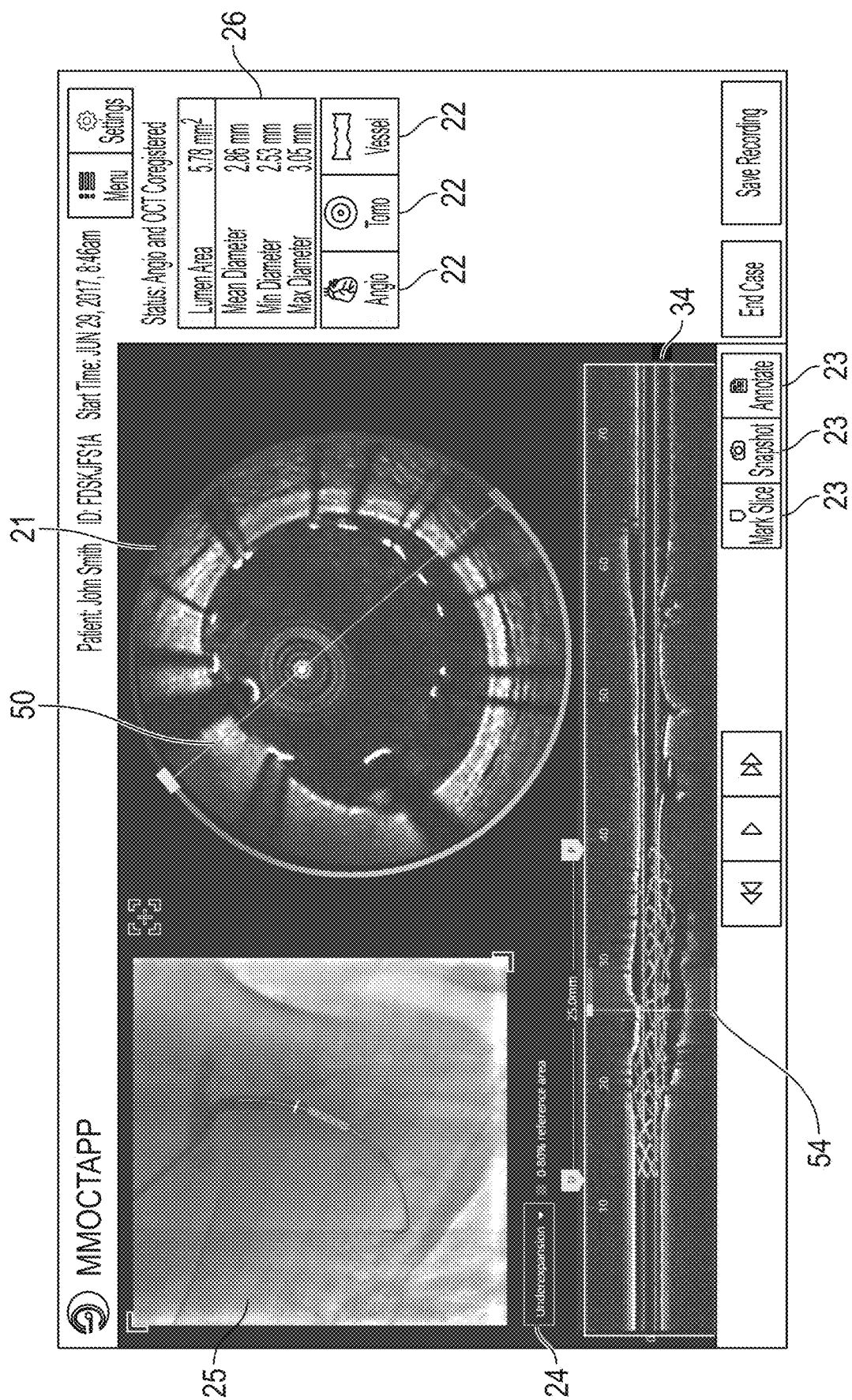
FIG. 10 shows at least one embodiment example of a GUI using an imaging modality which shows a cross-sectional, longitudinal vessel view in accordance with one or more aspects of the present disclosure.

One or more alternative embodiments may have the same or similar default display for IM1 30 and IM6 35—its user input, calculations, and updated display from one or more of the aforementioned embodiments (see e.g., FIGS. 2-8B, FIG. 9, etc.), and further shows IM5 34 which shows the cross-sectional, longitudinal vessel view having CB5 54 therein (e.g., instead of IM2 31 and IM3 32) as shown, for example, in FIG. 10.

A further embodiment may have the same default display, user input, calculations, and updated display from one or more of the aforementioned embodiments (see e.g., at least FIGS. 2-8B, FIG. 9, FIG. 10, etc.), except NS1 40 shows a semi-circle of NIRAF data instead of the full circle of NIRAF data around the OCT image 21, as shown, for example, in FIG. 11.

Figure 12:
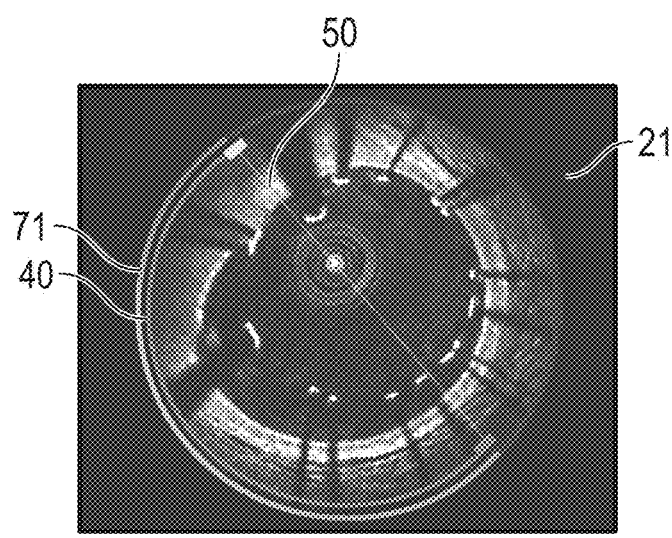

By way of another example of an alternative embodiment, FIG. 12 shows a partial view of at least one embodiment that may have the same default display, user input, calculations, and updated display from one or more of the aforementioned embodiments (see e.g., at least FIGS. 2-8B, FIG. 9, FIG. 10, FIG. 11, etc.), except NS1 40 shows a semi-circle 70 of NIRAF data inside the full circle 71 of NIRAF data around the OCT image 21. (See FIG. 12).

Figure 13:
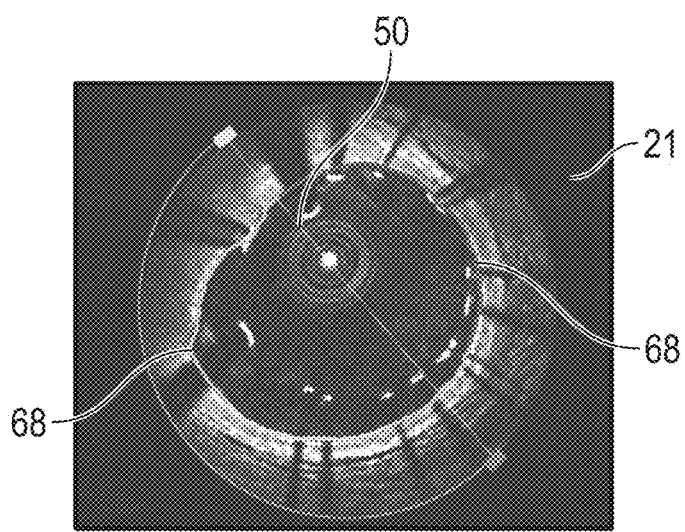

By way of a further example of another alternative embodiment, FIG. 13 shows a partial view of at least one embodiment that may have the same default display, user input, calculations, and updated display from one or more of the aforementioned embodiments (see e.g., at least FIGS. 2-8B, FIG. 9, FIG. 10, FIG. 11, FIG. 12, etc.), except the NIRAF data is merged and overlaid on top of the lumen edge 68. (See FIG. 13).

Figure 14:
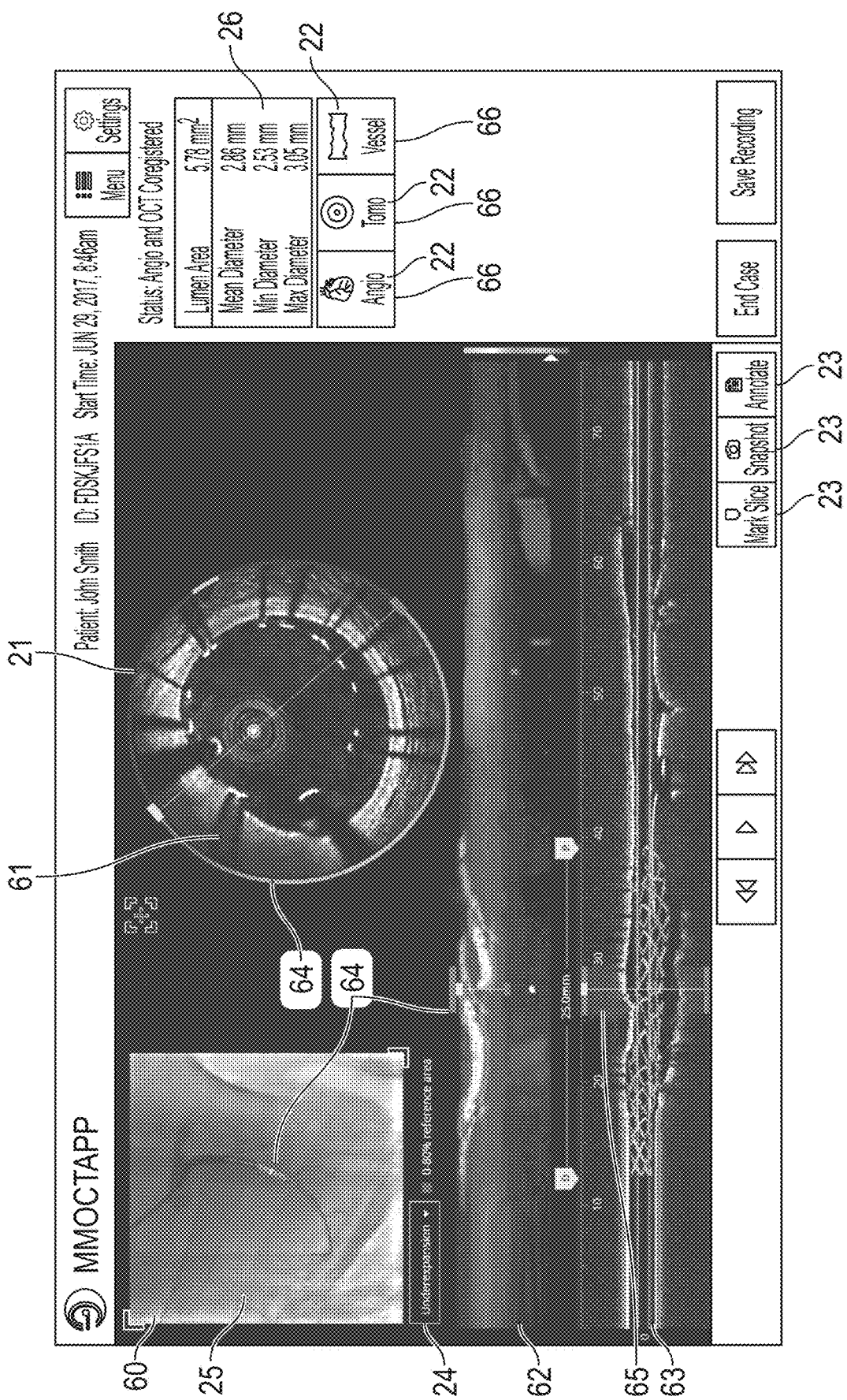
FIG. 14 shows at least one embodiment example of a GUI using multiple imaging modalities for an angiography device or system in accordance with one or more aspects of the present disclosure.

In addition to the standard tomographic view, the user may select to display multiple longitudinal views. When connected to an angiography system, the Graphical User Interface (GUI) may also display angiography images. FIG. 14 illustrates one example of a graphical user interface for the above embodiments. F1 60 may be an angiography view (e.g., an external feed), such as, but not limited to, the angiography image 25 discussed above. F2 61 may be a tomographic view, such as, but not limited to, the tomo or tomographic view, or OCT image, 21 discussed above. F3 62 may be a NIRAF carpet view as discussed above. F4 63 may be a simple longitudinal view. F5 64 illustrates that a NIRAF intensity may be displayed in multiple views. F6 65 may represent a stent under-expansion in one or more embodiments. F7 66 displays controls that may be used for customizing views, including, but not limited to, features 22, features 23, features 24, features 26, etc. as discussed above.

In accordance with one or more aspects of the present disclosure, the aforementioned features are not limited to being displayed or controlled using any particular GUI. In general, the aforementioned imaging modalities may be used in various ways, including with or without one or more features of aforementioned embodiments of a GUI. For example, Imaging Modality 1 (IM1) 30 may show the OCT image 21 with a tool to change the image view as aforementioned even if not presented with a GUI (or with one or more other components of a GUI; in one or more embodiments, the display may be simplified for a user to display set or desired information). This tool may be comprised of a Rotational Control Bar (CB1) 50 as aforementioned. In one or more embodiments, CB1 50 may have 2 handle bars and a circle in the center, which is overlaid and merged with half of the NIRAF data in a display. The control bar (CB1) can be moved bi-directionally, in a circular rotation, and the 2 handles are endpoints that may bound the color extremes of the NIRAF data or may correspondent to a cut or area displayed in a 3D view. One or more embodiments of CB1 50 may have one handle bar.

By way of another example, Imaging Modality 2 (IM2) 31 may show NIRAF data (NS2A 41A) displayed as a carpet view as aforementioned (with or without one or more features of aforementioned embodiments of a GUI). Control Bar (CB2) 51 may be used, and CB 2 51 may have 2 handle bars and may be displayed on half of the carpet view, matching the half of NS1 40 around IM1 30. CB 2 51 may be moved bi-directionally, horizontally as aforementioned. NIRAF signal gauge (NS2B) highlights the greatest NIRAF signal intensity using an arrow, matching the highlighted half of the NS1 40 around IM1 30. One or more embodiments of CB2 51 may have one handle bar.

By way of a further example, Imaging Modality 3 (IM3) 32 may show a reconstructed 3D, half pipe vessel view with a control bar to change the image view as aforementioned (with or without one or more features of aforementioned embodiments of a GUI). The half pipe vessel view may match the highlighted half of the NS1 40 around IM1 30. The NIRAF data (NS3) 42 may be displayed on the inner wall of IM3 32 and Control Bar (CB3) 52, with 2 handle bars, as displayed on IM3 32, matching the half of NS1 40 around IM1 30. One or more embodiments of CB3 52 may have one handle bar.

Imaging Modality (IM6) 35 may show the angiography image 25 with NIRAF data (NS6) 43 displayed along the vessel as aforementioned (with or without one or more features of aforementioned embodiments of a GUI). Control Bar (CB6) 55 may appear horizontally along the vessel of the angiography image.

Imaging Modality 1 (IM1) 30 may additionally show NIRAF data (NS1) 40 displayed in a full circle around the outer edge of the OCT image 21 as part of a rotational control bar, or as part of the OCT image 21 without a control bar. Another possible view in IM1 30, is one in which control bar CB1 may be merged with half of the NIRAF data with only half of the NIRAF data displayed. This tool may be moved bi-directionally, in a circular rotation; where the 2 handles are endpoints that bound the color extremes of the NIRAF data in one or more embodiments.

Imaging Modality 4 (IM4) 33 may also show the lumen diameter in the vessel view, instead of IM2 31 and IM3 32.

The procedure to select the region of interest and the position of the semi-circle, for example, using a touch screen, a GUI (or one or more components of a GUI; in one or more embodiments, the display may be simplified for a user to display the set or desired information), a processor (e.g., processor or computer 2, 1200, 1200', or any other processor discussed herein) may involve, in one or more embodiments, a single press with a finger and dragging on the area to move the semi-circle. The new orientation and updates to the view may be calculated upon release of a finger, or a pointer, such as the pointer 37 (see e.g., at least FIG. 3 as discussed above).

For one or more embodiments using a touch screen, two simultaneous touch points made around the tomo view may re-draw the semi-circle, where both handles align near or on the arc based on the two touch points, and then may adjust the orientation of the touch points, the arc and/or the semi-circle, and may update the view based on calculations upon release.

Additionally, for one or more embodiments using a touch screen, two simultaneous touch points may be made around the tomo image, with the fingers or pointer(s) held in place a sweeping motion around the tomo image in a circular motion that may move the rotational control bar (for example, only for Control Bar 1 50 on tomo view in one or more embodiments), and then may adjust the orientation of the touch points, the arc and/or the semi-circle, and may update the view based on calculations upon release.

When any control bar is moved bi-directionally, all other imaging modalities may update the display according to a specific moment in time selected by the user in one or more embodiments. In one or more embodiments, data may be primarily focused and controlled on IM1 30 by using CB1 50.

When control bar CB1 50 changes position on IM1 30, by being moved bi-directionally, rotating in a circular motion around the OCT image 21 via user input (see e.g., FIG. 3 as aforementioned), the following calculations may be performed in one or more embodiments:

1) On IM1 30, detect a catheter circumference, find a center of the catheter and/or circumference of the catheter, and draw a dot at the center location.
2) Draw through the catheter center point to create a diagonal line at an angle to the edges of the outer circle of the OCT image 21 to create an arc. In one or more embodiments, the arc represents a predetermined portion of the longitudinal view, such as, half of the longitudinal view (see e.g., FIGS. 5A-5B).
3) Determine active imaging modalities (e.g., IM1 30, IM2 31, IM3 32, and IM6 35; IM 4 33; IM5 34; etc.).
4) Calculate new orientation/position of control bars (e.g., CB1 50, CB2 51, CB3 52, and CB6 55; CB4 53; CB5 54; etc.) and active imaging modalities (e.g., IM1 30, IM2 31, IM3 32, and IM6 35; IM 4 33; IM5 34; etc.).

When calculations are complete, an updated display, or updating a display, may include one or more of the following:

1) Control Bar (e.g., CB1 50, CB2 51, CB3 52, and CB6 55; CB4 53; CB5 54; etc.) positions are updated within each imaging modality;
2) NS2A 41A, NS3 42, and NS6 43 will update NIRAF data and change display;
3) IM2 31 will scroll vertically, update NIRAF data and change display;
4) IM3 32 will scroll vertically, and update the 3D, half pipe vessel view with NIRAF data overlaid on the vessel; and
5) NS2B 41B will re-position the arrow to highlight the greatest NIRAF signal intensity matching to highlighted half of NIRAF ring.

When CB2 51 changes position on IM2 31 when moved bi-directionally, dragged horizontally (left and/or right) on the NIRAF carpet view (see e.g., FIG. 4), the same calculations may be performed as described in one or more of the aforementioned embodiments.

When CB2 51 changes position on IM2 31 when the bottom handle bar is pulled vertically downward, CB1 50 on IM1 30 may change the NIRAF data and update the display (see e.g., FIGS. 8A-8B).

In one or more embodiments, as a handle on the control bar on the tomo view is pulled in the opposite direction of the arc, the arc becomes larger and the field of view of the tomo image becomes larger. As a marker on the control bar (see e.g., CB1 50) is both pulled closer towards the arc on the tomo view—(e.g., towards the center of the tomo image, such as OCT image 21), the arc becomes smaller and the field of view and/or the image size of the tomo image, such as OCT image 21, becomes smaller.

In one or more embodiments, selecting the center dot of the rotational bar and expanding it out may change the shape of the arc, where the left and right of the new dot location may round and connect to the dot upon release. In one or more embodiments, the arc may change automatically based on the new dot placement to be sized and shaped according to that dot placement (for example, if the new dot placement increases or decreases the radius of the arc or semicircle (or changes a dimension of another geometric shape being used), then the arc adjusts accordingly). The NIRAF color extreme may also update to display on the rotational bar, based on the new shape. The bottom marker of the control bar may be expanded downward to also show the carpet view of the vessel, relative to the extent the arc area covers on the tomo image, such as the OCT image 21.

Additionally, a view that shows all the slices where malapposition/underexpansion occur with an overlap of NIRAF color extreme, may allow the user to jump to a region of choice in one or more embodiments.

One or more functions are controlled with the OCT image (e.g., such as the OCT image 21) view to centralize user attention, maintain focus, and allow the user to see all relevant information in a single moment in time. As aforementioned, functions extend across multi-modalities to provide more detailed information with, but not limited to, the NIRAF carpet view, 3D half pipe vessel view, lumen diameter, cross-sectional longitudinal view, etc. In one or more embodiments displays are configurable.

In one or more embodiments, multiple imaging modalities are displayed. For example, an OCT and a NIRAF tomo view may be combined. There may be an OCT and NIRAF ring around and outside of the tomo view (e.g., see OCT view 21). In one or more embodiments, the OCT and NIRAF data may be merged on an inner lumen edge. The OCT and NIRAF data may be splayed (i.e., in a full view, in a partial (semi-circle or other geometric shape) view, etc. OCT and NIRAF may be on longitudinal (cross-sectional view/raw data) display. OCT and NIRAF data may be on a 3D, half-pipe view as aforementioned. OCT and NIRAF data may be displayed on a 3D, half-pipe view and a NIRAF carpet view together.

In one or more embodiments, one or more control bars may be used as described above to view, control, modify, emphasize, etc. one or more of the imaging modalities. For example, a moveable control bar may be included for one or more of (if not all of) the views in the GUI, including, but not limited to, the tomo view (see e.g., OCT image 21), the NIRAF carpet view, the longitudinal (cross-sectional view/raw data) view, the lumen profile, and the 3D, half-pipe view, etc. An arc on the control bar may indicate a predetermined portion (e.g., half) of the cross-sectional tomo view. One or more control bars may have one or two handles at respective ends thereof. In an embodiment having two handles for a control bar, the two handles may operate as endpoints that are draggable (capable of being dragged or moved) in: (i) a circular, rotational direction on a particular view, such as, the tomo view (see e.g., OCT view 21); and/or (ii) in a horizontal direction for a particular view, such as, on the NIRAF carpet view, longitudinal (cross-sectional view), 3D half pipe view, lumen profile view, etc. The two handles may operate as endpoints that bound the color extremes of the NIRAF data. In a tomo view (e.g., OCT view 21) for example, the two handles (see e.g., the handles 36A, 36B as discussed above for FIG. 3) may utilize a touch functionality. A control bar on a NIRAF carpet view and on a longitudinal view may be moveable, such that the respective control bar moves from left to right (and/or right to left) and/or a user may select the desired control bar to move to a specific image position.

One or more procedures may be used in one or more embodiments to select a region of choice or a region of interest and to position the semi-circle (or other geometrically shaped) area for a view. For example, after a single touch is made on a selected area (e.g., by using a touch screen, by using a mouse or other input device to make a selection, etc.), the semi-circle (or other geometric shape used for the designated area) may automatically adjust to the selected region of choice or interest. Two (2) single touch points may operate to connect/draw the region of choice or interest. A single touch on a tomo view (e.g., the OCT view 21) may operate to sweep around the tomo view, and may connect to form the region of choice or interest. Two fingers or pointers may be used to rotate a control bar (e.g., for CB1 50 on a tomo view shown, for example, in at least FIG. 2 or FIG. 3). In at least one embodiment for a NIRAF carpet view, when a bottom handle is pulled vertically downward, a rotational control bar on the tomo view may become greater than 180 degrees).

One or more embodiments may share or have different features than those features discussed above. For example, a NIRAF data color map or view may be merged with a rotational half circle (arc) as discussed above (see e.g., FIG. 11 discussed above). As a control bar (e.g., CB1 50) is rotated on the tomo view (e.g., view 21), the NIRAF color extreme may change according to the collected NIRAF data, and/or the NIRAF carpet view may scroll vertically and simultaneously update the data. As a control bar or control bars on a NIRAF carpet view and longitudinal view moves/move from left to right (and/or right to left), the indicator on a gauge (see e.g., the gauge 41B) may show which color extreme is most visible at a specific image position. As a control bar (e.g., CB1 50) is rotated on the tomo view (e.g., view 21), the longitudinal view (cross-sectional view), 3D, half-pipe view may scroll vertically and simultaneously update the data. As a control bar (e.g., CB1 50) is rotated on the tomo view (e.g., view 21), the NIRAF carpet view may stay stationary, where the handles (e.g., the handles 36A, 36B) of a control bar (e.g., CB1 50, CB2 51, CB3 52, etc.) may be adjustable (e.g., from half to full vessel). As a handle on the control bar on the tomo view is pulled in the opposite direction of the arc, the arc may become larger and the field of view of the tomo image may become larger. As a marker on the control bar is both pulled closer towards the arc on the tomo view—towards the center of the tomo image, the arc becomes smaller and the field of view of the tomo image becomes smaller.

In one or more embodiments, a method for switching between a semi-circle (or part of another geometric shape) to a full circle (or a complete version of the another geometric shape) or vice versa may be used. For example, when switching between a semi-circle and a full circle or vice versa, a user may select a center dot of the rotational control bar and expand it out to change the shape of the arc, where the left and right of the new dot location will round and connect to the dot upon release. For example, if a user wants to set the control bar1 50 such that it captures all of the data for the OCT image 21, then, in one or more embodiments, the 3D view may be a full pipe view (showing the entire circle). The NIRAF color extreme may also be updated to display on the rotational control bar, based on the new or changed shape. A bottom marker of the control bar may be expanded downward to also show the carpet view of the vessel, relative to the extent the arc area covers on the tomo image.

Figure 15A:
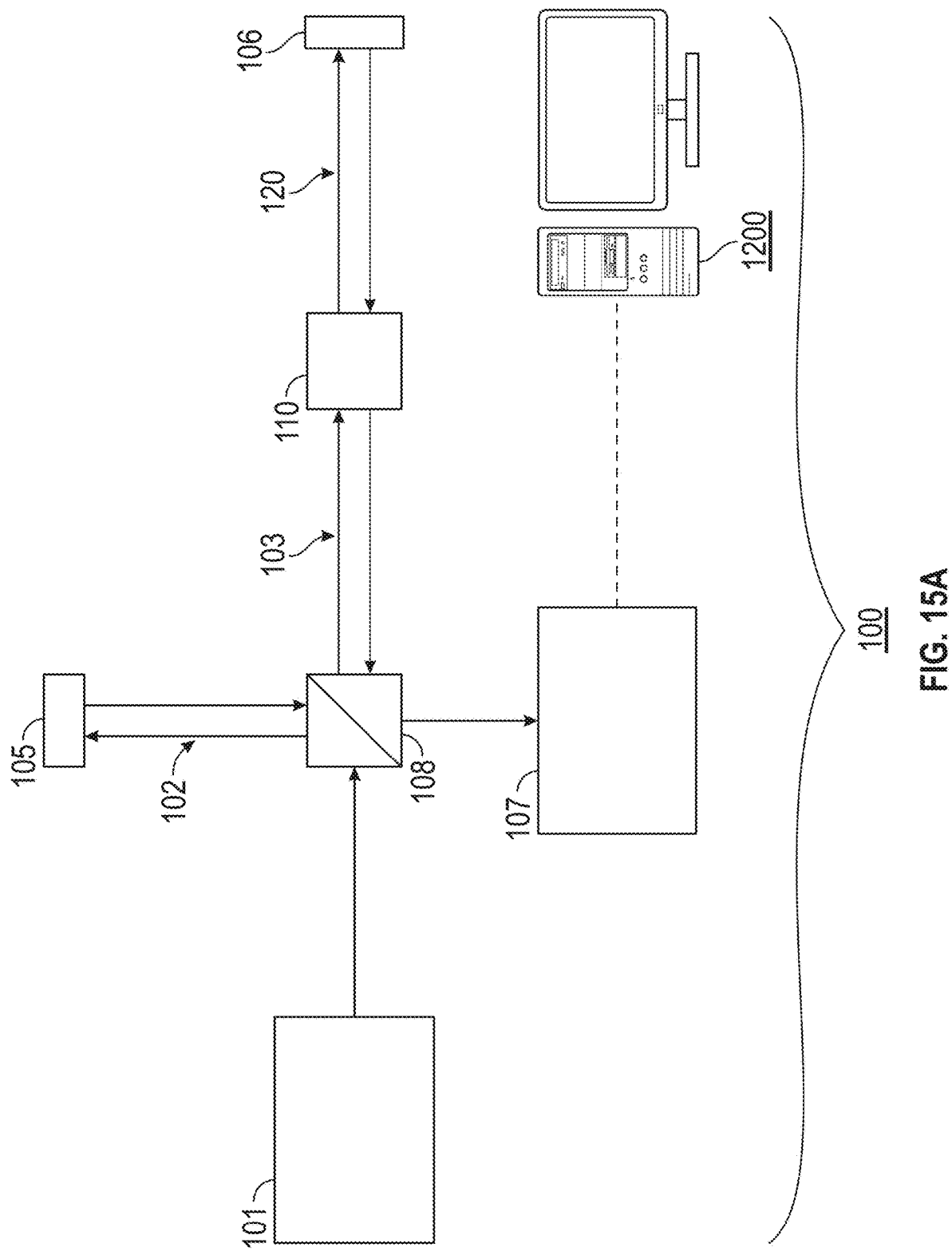
FIG. 15A shows at least one embodiment of an OCT apparatus or system for utilizing multiple imaging modalities in accordance with one or more aspects of the present disclosure.

FIG. 15A shows an OCT system 100 (as referred to herein as "system 100" or "the system 100") which may be used for multiple imaging modalities in accordance with one or more aspects of the present disclosure. The system 100 comprises a light source 101, a reference arm 102, a sample arm 103, a deflected or deflecting section 108, a reference mirror (also referred to as a "reference reflection", "reference reflector", "partially reflecting mirror" and a "partial reflector") 105, and one or more detectors 107 (which may be connected to a computer 1200). In one or more embodiments, the system 100 may include a patient interface device or unit ("PIU") no and a catheter 120 (see e.g., embodiment examples of a PIU and a catheter as shown in FIG. 1 and FIGS. 15A-15C), and the system 100 may interact with a sample, object, patient (e.g., a blood vessel of a patient), target 106 (e.g., via the catheter 120 and/or the PIU 110). In one or more embodiments, the system 100 includes an interferometer or an interferometer is defined by one or more components of the system 100, such as, but not limited to, at least the light source 101, the reference arm 102, the sample arm 103, the deflecting section 108 and the reference mirror 105.

Figure 15B:
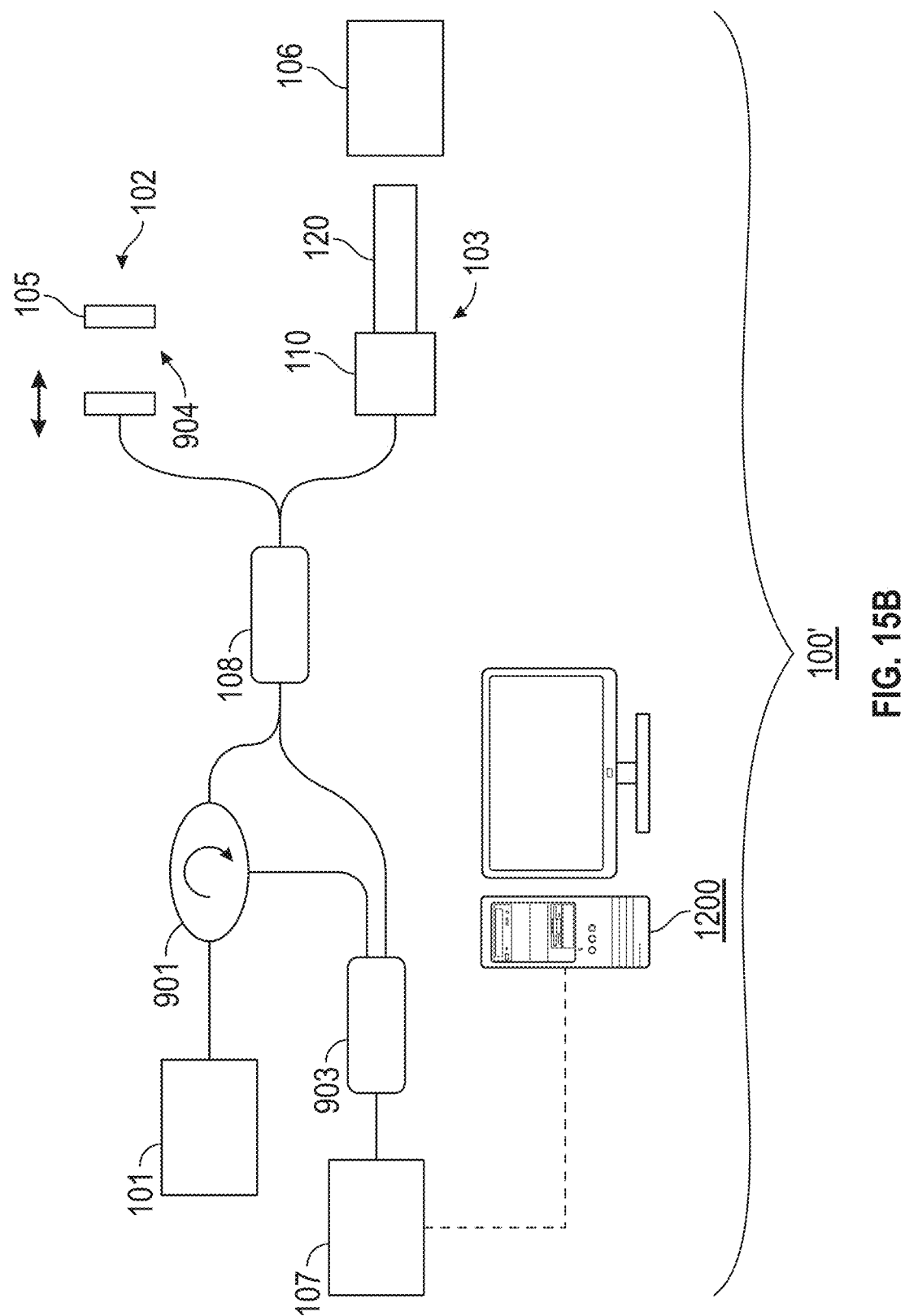
FIG. 15B shows at least another embodiment of an OCT apparatus or system for utilizing multiple imaging modalities in accordance with one or more aspects of the present disclosure.

In accordance with one or more further aspects of the present disclosure, bench top systems may be utilized with multiple imaging modalities as disclosed herein. FIG. 15B shows an example of a system that can utilize the multiple imaging modalities and related methods discussed herein for a bench-top such as for ophthalmic applications. A light from a light source 101 delivers and splits into a reference arm 102 and a sample arm 103 with a deflecting section 108. A reference beam goes through a length adjustment section 904 and is reflected from a reference mirror (such as or similar to the reference mirror or reference reflection 105 shown in FIG. 15A) in the reference arm 102 while a sample beam is reflected or scattered from a sample, target, object, patient (e.g., blood vessel of a patient), etc. 106 in the sample arm 103 (e.g., via the PIU 110 and the catheter 120). In one embodiment, both beams combine at the deflecting section 108 and generate interference patterns. In one or more embodiments, the beams go to the combiner 903, and the combiner 903 combines both beams via the circulator 901 and the deflecting section 108, and the combined beams are delivered to one or more detectors (such as the one or more detectors 107). The output of the interferometer is continuously acquired with one or more detectors, such as the one or more detectors 107. The electrical analog signals are converted to the digital signals to analyze them with a computer, such as, but not limited to, the computer 1200 (see FIGS. 15A-15C; also shown in FIG. 17 discussed further below), the computer 1200' (see e.g., FIG. 18 discussed further below), etc. Additionally or alternatively, one or more of the computers, CPUs, processors, etc. discussed herein may be used to process, control, update, emphasize, and/or change one or more of the multiple imaging modalities, and/or process the related techniques, functions or methods, or may process the electrical signals as discussed above.

Figure 15C:
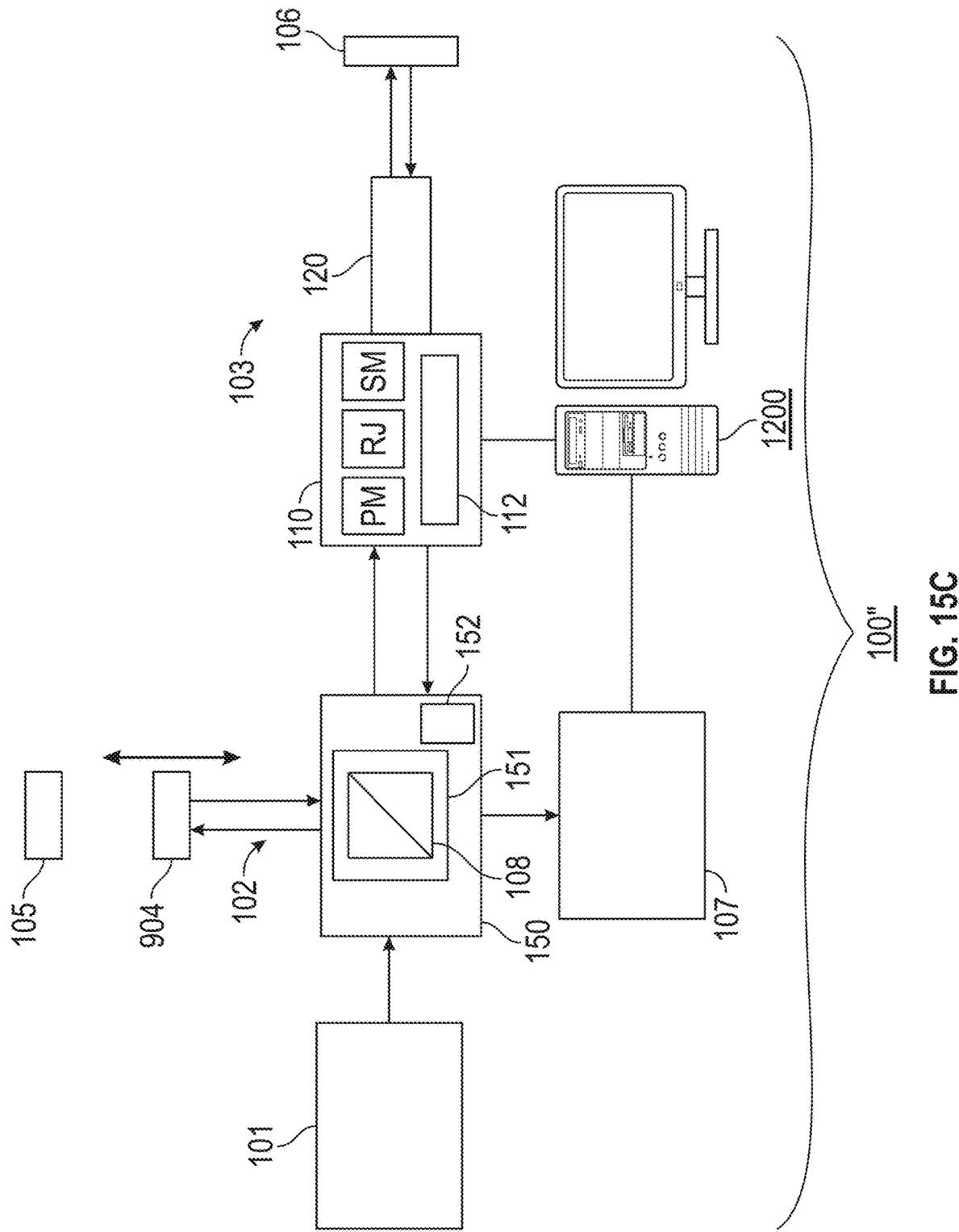
FIG. 15C shows at least a further embodiment of an OCT apparatus or system for utilizing multiple imaging modalities in accordance with one or more aspects of the present disclosure.

In accordance with one or more further aspects of the present disclosure, one or more other systems may be utilized with one or more of the multiple imaging modalities and related method(s) as disclosed herein. FIG. 15C shows an example of a system 100" that may utilize the one or more multiple imaging modalities and/or related technique(s) or method(s) such as for ophthalmic applications. A light from a light source 101 delivers and splits into a reference arm 102 and a sample arm 103 with a deflecting section 108 (e.g., a beamsplitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may go or pass through a length adjustment section 904, which may operate to change the distance of a reference mirror (such as reference mirror or reference reflection 105; also shown in FIG. 15A for example) and is reflected from the reference reflection 105 in the reference arm 102 while a sample beam is reflected or scattered from a sample, target, object, patient (e.g., blood vessel of a patient), etc. 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see FIGS. 15A-15C; also shown in FIG. 17 discussed further below), the computer 1200' (see e.g., FIG. 18 discussed further below), etc. Additionally or alternatively, one or more of the computers, CPUs, processors, etc. discussed herein may be used to process, control, update, emphasize, and/or change one or more of the multiple imaging modalities, and/or process the related techniques, functions or methods, or may process the electrical signals as discussed above. In one or more embodiments, the sample arm 103 includes the PIU 110 and the catheter 120 so that the sample beam is reflected or scattered from the sample, target, object, patient (e.g., blood vessel of a patient), etc. 106 as discussed herein. In one or more embodiments, the PIU 110 may include one or more motors to control the pullback operation of the catheter 120

(or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. As discussed herein, the PIU 110 may include a rotary junction (e.g., rotary junction RJ as shown in FIG. 15C). The rotary junction RJ may be connected to the spin motor SM so that the catheter 120 may obtain one or more views or images of the sample, target, object, patient (e.g., blood vessel of a patient), etc. 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

Preferably, in one or more embodiments including the deflecting or deflected section 108 (best seen in FIGS. 15A-15C), the deflected section 108 operates to deflect the light from the light source 101 to the reference arm 102 and/or the sample arm 103, and then send light received from the reference arm 102 and/or the sample arm 103 towards the at least one detector 107 (e.g., a spectrometer, one or more components of the spectrometer, another type of detector, etc.). In one or more embodiments, the deflected section (e.g., the deflected section 108 of the system 100, 100', 100", any other system discussed herein, etc.) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 (or any other system discussed herein) such as, but not limited to, one or more of the light source 101, the deflected section 108, the rotary junction RJ, a PIU 110, a catheter 120, etc. One or more features of the aforementioned configurations of at least FIGS. 1-15C may be incorporated into one or more of the systems, including, but not limited to, the system 100, 100', 100", discussed herein.

While not limited to such arrangements, configurations, devices or systems, one or more embodiments of the devices, apparatuses, systems, methods, storage mediums, GUI's, etc. discussed herein may be used with an apparatus or system as aforementioned, such as, but not limited to, for example, the system 100, the system 100', the system 100", the devices, apparatuses, or systems of FIGS. 1-15C, any other device, apparatus or system discussed herein, etc. In one or more embodiments, one user may perform the method(s) discussed herein. In one or more embodiments, one or more users may perform the method(s) discussed herein. In one or more embodiments, one or more of the computers, CPUs, processors, etc. discussed herein may be used to process, control, update, emphasize, and/or change one or more of the multiple imaging modalities, and/or process the related techniques, functions or methods, or may process the electrical signals as discussed above.

The light source 101 may include a plurality of light sources or may be a single light source. The light source 101 may be a broadband lightsource, and may include one or more of a laser, an organic light emitting diode (OLED), a light emitting diode (LED), a halogen lamp, an incandescent lamp, supercontinuum light source pumped by a laser, and/or a fluorescent lamp. The light source 101 may be any light source that provides light which may then be dispersed to provide light which is then used for imaging, performing control, viewing, changing, emphasizing methods for multiple imaging modalities and/or any other method discussed herein. The light source 101 may be fiber coupled or may be free space coupled to the other components of the apparatus and/or system 100, 100', 100", the devices, apparatuses or systems of FIGS. 1-15C, or any other embodiment discussed herein. As aforementioned, the light source 101 may be a swept-source (SS) light source.

Additionally or alternatively, the one or more detectors 107 may be a linear array, a charge-coupled device (CCD), a plurality of photodiodes or some other method of converting the light into an electrical signal. The detector(s) 107 may include an analog to digital converter (ADC). The one or more detectors may be detectors having structure as shown in one or more of FIGS. 1-15C and as discussed above.

Figure 16:
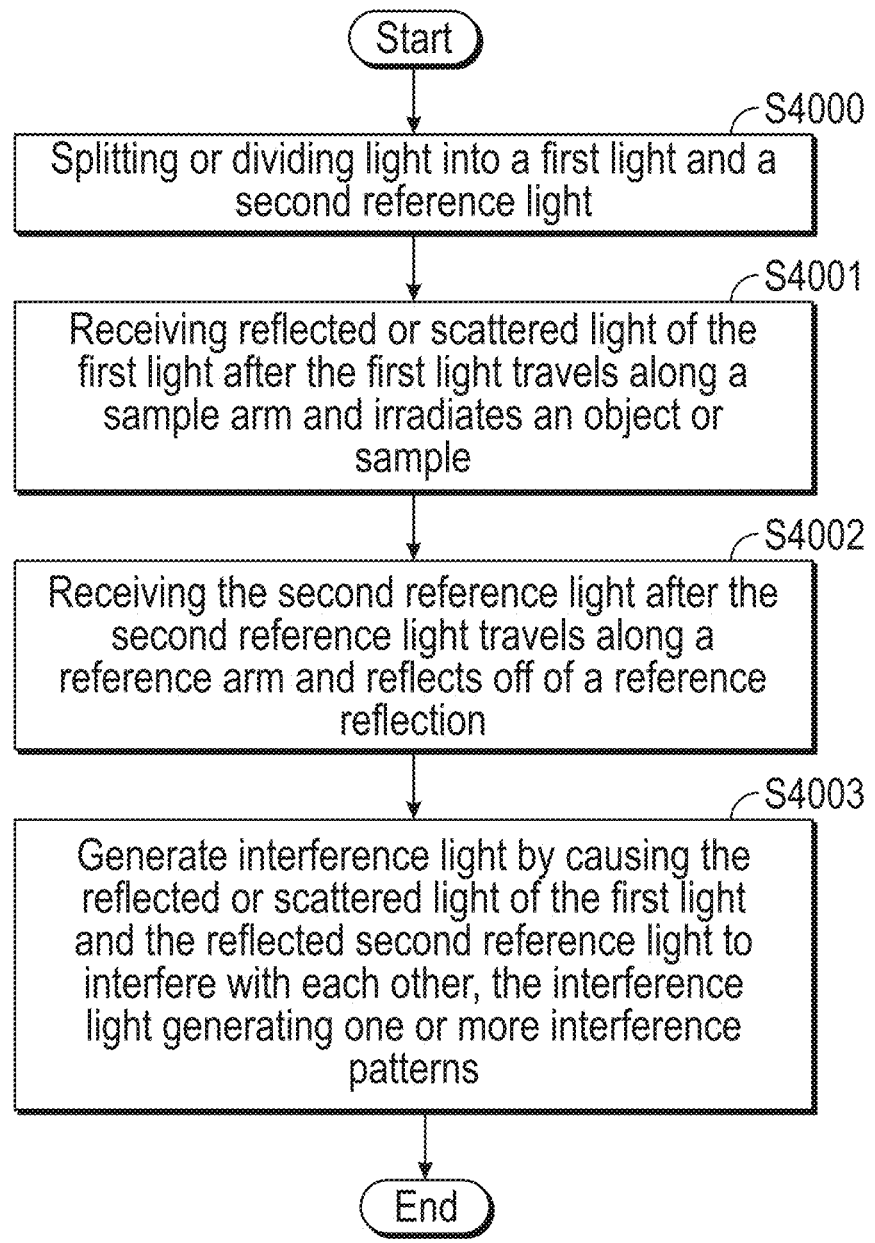
FIG. 16 is a flow diagram showing a method of performing an imaging feature, function or technique in accordance with one or more aspects of the present disclosure.

In accordance with one or more aspects of the present disclosure, one or more methods for performing imaging are provided herein. FIG. 16 illustrates a flow chart of at least one embodiment of a method for performing imaging. Preferably, the method(s) may include one or more of the following: (i) splitting or dividing light into a first light and a second reference light (see step S4000 in FIG. 16); (ii) receiving reflected or scattered light of the first light after the first light travels along a sample arm and irradiates an object or a sample (see step S4001 in FIG. 16); (iii) receiving the second reference light after the second reference light travels along a reference arm and reflects off of a reference reflection (see step S4002 in FIG. 16); and generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 16). One or more methods may further include using low frequency monitors to update or control high frequency content to improve image quality. For example, one or more embodiments may use multiple imaging modalities, related methods or techniques for same, etc. to achieve improved image quality. In one or more embodiments, an imaging probe may be connected to one or more systems (e.g., the system 100, the system 100', the system 100", the devices, apparatuses or systems of FIGS. 1-18, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

The one or more detectors 107 may transmit the digital or analog signals to a processor or a computer such as, but not limited to, an image processor, a processor or computer 1200, 1200' (see e.g., FIGS. 15A-15C and 17-18), a combination thereof, etc. The image processor may be a dedicated image processor or a general purpose processor that is configured to process images. In at least one embodiment, the computer 1200, 1200' may be used in place of, or in addition to, the image processor. In an alternative embodiment, the image processor may include an ADC and receive analog signals from the one or more detectors 107. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the devices, apparatuses or systems of FIGS. 1-15C, the computer 1200, the computer 1200', the image processor, may also include one or more components further discussed herein below (see e.g., FIGS. 17-18).

In at least one embodiment, a console or computer 1200, 1200' operates to control motions of the RJ via the motion control unit (MCU) 112 or a motor M, acquires intensity data from the detector(s) in the one or more detectors 107, and displays the scanned image (e.g., on a monitor or screen such as a display, screen or monitor 1209 as shown in the console or computer 1200 of any of FIGS. 15A-15C and FIG. 17 and/or the console 1200' of FIG. 18 as further discussed below). In one or more embodiments, the MCU 112 or the motor M operates to change a speed of a motor of the RJ and/or of the RJ. The motor may be a stepping or a DC servo motor to control the speed and increase position accuracy (e.g., compared to when not using a motor, compared to when not using an automated or controlled speed and/or position change device, compared to a manual control, etc.).

The output of the one or more components of any of the systems discussed herein may be acquired with the at least one detector 107, e.g., such as, but not limited to, photodiodes, Photomultiplier tube(s) (PMTs), line scan camera(s), or multi-array camera(s). Electrical analog signals obtained from the output of the system 100, 100', 100", and/or the detector(s) 107 thereof, and/or from the devices, apparatuses, or systems of FIGS. 1-15C, are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Unless otherwise discussed herein, like numerals indicate like elements. For example, while variations or differences exist between the systems, such as, but not limited to, the system 100, the system 100', the system 100", or any other device, apparatus or system discussed herein, one or more features thereof may be the same or similar to each other, such as, but not limited to, the light source 101 or other component(s) thereof (e.g., the console 1200, the console 1200', etc.). Those skilled in the art will appreciate that the light source 101, the motor or MCU 112, the RJ, the at least one detector 107, and/or one or more other elements of the system 100 may operate in the same or similar fashion to those like-numbered elements of one or more other systems, such as, but not limited to, the devices, apparatuses or systems of FIGS. 1-15C, the system 100', the system 100", or any other system discussed herein. Those skilled in the art will appreciate that alternative embodiments of the devices, apparatuses or systems of FIGS. 1-15C, the system 100', the system 100", any other device, apparatus or system discussed herein, etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100 of FIG. 15A and one or more embodiments shown in any of FIGS. 1-14 and 15B-15C, for example, as discussed herein, there are similarities. Likewise, while the console or computer 1200 may be used in one or more systems (e.g., the system 100, the system 100', the system 100", the devices, apparatuses or systems of any of FIGS. 1-18, or any other system discussed herein, etc.), one or more other consoles or computers, such as the console or computer 1200', may be used additionally or alternatively.

There are many ways to compute intensity, viscosity, resolution (including increasing resolution of one or more images), etc., and/or to use multiple imaging modalities, and/or related methods for same, discussed herein, digital as well as analog. In at least one embodiment, a computer, such as the console or computer 1200, 1200', may be dedicated to control and monitor the imaging (e.g., OCT, single mode OCT, multimodal OCT, multiple imaging modalities, etc.) devices, systems, methods and/or storage mediums described herein.

The electric signals used for imaging may be sent to one or more processors, such as, but not limited to, a computer or processor 2 (see e.g., FIG. 1), a computer 1200 (see e.g., FIGS. 15A-15C and 17), a computer 1200' (see e.g., FIG. 18), etc. as discussed further below, via cable(s) or wire(s), such as, but not limited to, the cable(s) or wire(s) 113 (see FIG. 17). Additionally or alternatively, the electric signals, as aforementioned, may be processed in one or more embodiments as discussed above by any other computer or processor or components thereof. The computer or processor 2 as shown in FIG. 1 may be used instead of any other computer or processor discussed herein (e.g., computer or processors 1200, 1200', etc.), and/or the computer or processor 1200, 1200' may be used instead of any other computer or processor discussed herein (e.g., computer or processor 2). In other words, the computers or processors discussed herein are interchangeable, and may operate to perform any of the multiple imaging modalities feature(s) and method(s) discussed herein, including using, controlling, and changing a GUI or multiple GUI's.

Figure 17:
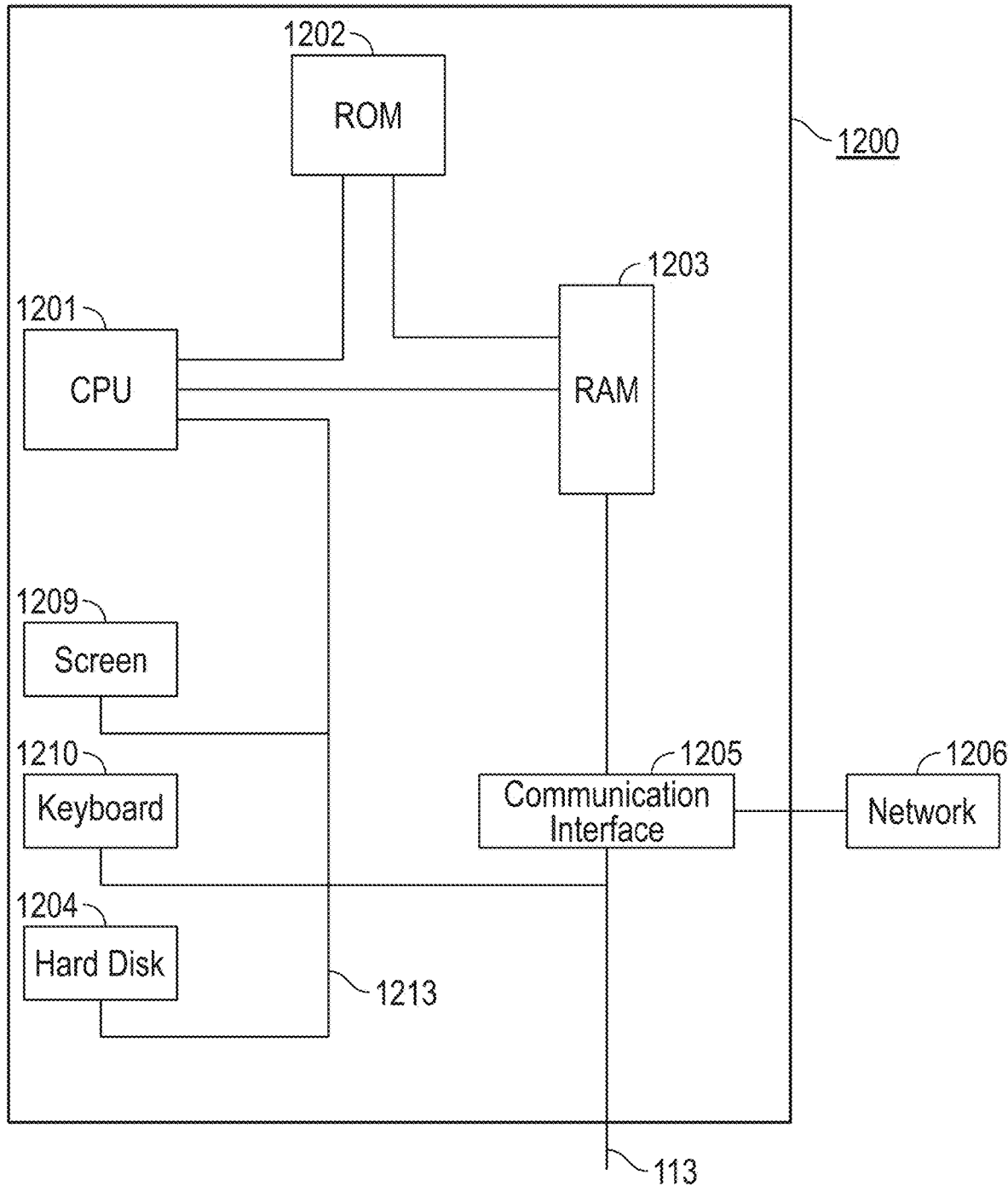
FIG. 17 shows a schematic diagram of an embodiment of a computer that may be used with one or more embodiments of an apparatus or system or one or more methods discussed herein in accordance with one or more aspects of the present disclosure.

Various components of a computer system 1200 are provided in FIG. 17. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS (or "Bus") or other connection lines (e.g., connection line 1213) between one or more of the aforementioned components (e.g., including but not limited to, being connected to the console, the probe, the imaging apparatus or system, any motor discussed herein, a light source, etc.). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a device or system, such as, but not limited to, an apparatus or system using one or more imaging modalities and related method(s) as discussed herein), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for tissue or sample characterization, diagnosis, evaluation and/or imaging. The system 1200 may further include one or more processors connected via a network connection (e.g., via network 1206). The CPU 1201 and any additional processor being used by the system 1200 may be located in the same telecom network or in different telecom networks (e.g., performing feature(s), function(s), technique(s), method(s), etc. discussed herein may be controlled remotely).

The I/O or communication interface 1205 provides communication interfaces to input and output devices, which may include a light source, a spectrometer, a microphone, a communication cable and a network (either wired or wireless), a keyboard 1210, a mouse (see e.g., the mouse 1211 as shown in FIG. 18), a touch screen or screen 1209, a light pen and so on. The communication interface of the computer 1200 may connect to other components discussed herein via line 113 (as diagrammatically shown in FIG. 17). The Monitor interface or screen 1209 provides communication interfaces thereto.

Any methods and/or data of the present disclosure, such as the methods for performing tissue or sample characterization, diagnosis, examination and/or imaging (including, but not limited to, increasing image resolution, performing imaging using multiple imaging modalities, viewing or changing one or more multiple imaging modalities and related methods (and/or option(s) or feature(s)), etc.), for example, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 18), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 17. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 17), the processor or computer 2 (as shown in FIG. 1) and/or the computer or processor 1200' (as shown in FIG. 18) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program (s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium. The computers or processors (e.g., 2, 1200, 1200', etc.) may include the aforementioned CPU structure, or may be connected to such CPU structure for communication therewith.

As aforementioned, hardware structure of an alternative embodiment of a computer or console 1200' is shown in FIG. 18. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with a motor, a console, or any other component of the device(s) or system(s) discussed herein via the operation interface 1214 or the network interface 1212 (e.g., via a cable or fiber, such as the cable or fiber 113 as similarly shown in FIG. 17). A computer, such as the computer 1200', may include a motor or motion control unit (MCU) in one or more embodiments. The operation interface 1214 is connected with an operation unit such as a mouse device 1211, a keyboard 1210 or a touch panel device. The computer 1200' may include two or more of each component.

At least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

The computer, such as the computer 2, the computer 1200, 1200', (or other component(s) such as, but not limited to, the PCU, etc.), etc. may communicate with an MCU, an interferometer, a spectrometer, a detector, etc. to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate any system discussed herein. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs any system discussed herein to set or change the imaging condition (e.g., improving resolution of an image or images), and to start or end the imaging. A light or laser source and a spectrometer and/or detector may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/ 0101374, and 2016/0228097, and WO 2016/144878, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. An imaging device comprising:
one or more processors that operate to:
display an image for each of multiple imaging modalities on a display;
receive an input request during a rotational, scrolling, or sliding movement of an interaction, performed on or performed using the display, with one or more of the displayed images where at least the display of the one or more images is changed during the interaction, and/or receive an input request during an interaction, performed on or performed using the display, with one or more moveable control bars or tools displayed on or in the one or more of the displayed images where the one or more moveable control bars or tools are rotationally moved or are scrolled or slid during the interaction to receive the input request, the input request operating to change the one or more of the displayed images of at least one of the multiple imaging modalities; and
synchronously update each displayed image for each of the multiple imaging modalities based on the received input request such that data is changed in each of the displays for each of the multiple imaging modalities based on the received input request and such that: (i) an orientation or position for each displayed image(s) for each of the other multiple imaging modalities is updated synchronously by rotating, scrolling, or sliding each of the displayed image(s) by an amount equal or corresponding to the rotational, scrolling, or sliding movement of the interaction and/or the moveable control bars or tools and displayed using the updated orientation or position based on the rotational, scrolling, or sliding movement of the interaction and/or the moveable control bars or tools, or (ii) a frame for each displayed image(s) for each of the other multiple imaging modalities is updated synchronously to be a different frame corresponding to or located at a position selected by the scrolling or sliding along a direction of an image of the one or more images where the movement is a scrolling or sliding movement and/or where the moveable control bars or tools are scrolled or slid,
wherein the one or more processors further operate to at least:
(i) determine whether at least one of two cases occurs, where a first case of the two cases is where the input request is received during the rotational, sliding, or scrolling movement of the interaction with a displayed image for one imaging modality of the multiple imaging modalities and where a second case of the two cases is where the input request is received during the interaction with one or more rotational, scrolling, or sliding moveable control bars or tools displayed on or in the displayed image for the one imaging modality of the multiple imaging modalities, and, where the first case and/or the second case of the two cases is/are determined to occur, perform the synchronous update for the other displayed image(s) for each of the multiple imaging modalities; and (ii) determine whether at least one of two other cases occurs, where a first other case of the two other cases is where the input request is received during the rotational, sliding, or scrolling movement of the interaction with a displayed image for another imaging modality of the multiple imaging modalities and where a second other case of the two other cases is where the input request is received during the interaction with one or more rotational, scrolling, or sliding moveable control bars or tools displayed on or in the displayed image for the another imaging modality of the multiple imaging modalities, and, where the first other case and/or the second other case of the two other cases is/are determined to occur, perform the synchronous update for the other displayed image(s) for each of the multiple imaging modalities, where the one imaging modality is different from the another imaging modality.

2. The imaging device of claim 1, wherein one or more of the following:

(i) the one or more processors further operate to update all of the multiple imaging modalities based on a specific moment in time based on when the input request is received or based on when the input request is selected or entered by a user;

(ii) the one or more processors further operate to display a control bar or tool of the one or more control bars or tools on or in at least a first imaging modality of the multiple imaging modalities, and to detect the input request based on a change performed to the control bar or tool;

(iii) the one or more processors further operate to display the one or more control bars or tools such that each control bar or tool of the one or more control bars or tools is displayed on or in an image for a respective imaging modality of the multiple imaging modalities and/or such that all displayed images for the multiple imaging modalities include a control bar or tool displayed on or in each respective displayed image of the displayed images, and to detect the input request based on a change performed to one of the control bars or tools;

(iv) the one or more processors further operate to one or more of: detect stent expansion or underexpansion, detect stent apposition or malapposition, perform co-registration of two or more imaging modalities of the multiple imaging modalities, perform imaging using at least one of the multiple imaging modalities, display a notification regarding the detected stent expansion or underexpansion, and display a notification regarding the detected stent apposition or malapposition;

(v) the one or more processors further operate at least one control bar or tool of the one or more control bars or tools to move bi-directionally based on the input request;

(vi) the one or more processors further operate at least one control bar or tool of the one or more control bars or tools to move bi-directionally based on the input request such that the bi-directional movement of the control bar or tool, or the one or more control bars or tools, is rotational, horizontal, vertical, parallel, or perpendicular to the control bar or tool or to the one or more control bars or tools, or along the control bar or tool or the one or more control bars or tools; and/or (vii) the one or more processors further operate to perform the synchronous update such that the input request operates to change two-dimensional (2D) and three-dimensional (3D) aspects or features in one or more images of the multiple imaging modalities.

3. The imaging device of claim 2, wherein one or more of the following:

(i) the multiple imaging modalities include two or more of the following modalities: an imaging modality for a tomography image, an imaging modality for an Optical Coherence Tomography (OCT) image, an imaging modality for a near-infrared fluorescence (NIRF) image, an imaging modality for a near-infrared auto-fluorescence (NIRAF) image, a near-infrared fluorescence (NIRF) imaging modality in a carpet view, a near-infrared auto-fluorescence (NIRAF) imaging modality in a carpet view, an imaging modality for a three-dimensional (3D) rendering, an imaging modality for a 3D rendering of a vessel, an imaging modality for a 3D rendering of a vessel in a half-pipe view or display, an imaging modality for a lumen profile, an imaging modality for a lumen diameter display, an imaging modality for a longitudinal view, and an imaging modality for an angiography view;

(ii) the display device displays the images of the multiple imaging modalities as one or more of the following: a tomography image of a lumen, an Optical Coherence Tomography (OCT) image of a lumen, a near-infrared auto-fluorescence (NIRAF) image of a lumen, a near-infrared auto-fluorescence (NIRAF) image of a lumen in a carpet view, a near-infrared fluorescence (NIRF) image of a lumen, a near-infrared fluorescence (NIRF) image of a lumen in a carpet view, a three-dimensional (3D) rendering of a lumen, a 3D rendering of a vessel, a 3D rendering of a vessel in a half-pipe view, a lumen profile view, a lumen diameter view, a longitudinal cross-sectional view of a lumen, and an angiography view of a lumen;

(iii) the multiple imaging modalities include three or more of the following modalities: an imaging modality for a tomography image, an Optical Coherence Tomography (OCT) image modality, a near-infrared fluorescence (NIRF) image modality, a near-infrared auto-fluorescence (NIRAF) imaging modality, a near-infrared fluorescence (NIRF) imaging modality in a carpet view, a near-infrared auto-fluorescence (NIRAF) imaging modality in a carpet view, an imaging modality for a three-dimensional (3D) rendering, an imaging modality for a 3D rendering of a vessel, an imaging modality for a 3D rendering of a vessel in a half-pipe view or display, an imaging modality for a lumen profile, an imaging modality for a lumen diameter display, an imaging modality for a longitudinal view, and an imaging modality for an angiography view; and/or (iv) the multiple imaging modalities include four or more of the following modalities: an imaging modality for a tomography image, an Optical Coherence Tomography (OCT) image modality, a near-infrared fluorescence (NIRF) image modality, a near-infrared auto-fluorescence (NIRAF) imaging modality, a near-infrared fluorescence (NIRF) imaging modality in a carpet view, a near-infrared auto-fluorescence (NIRAF) imaging modality in a carpet view, an imaging modality for a three-dimensional (3D) rendering, an imaging modality for a 3D rendering of a vessel, an imaging modality for a 3D rendering of a vessel in a half-pipe view or display, an imaging modality for a lumen profile, an imaging modality for a lumen diameter display, an imaging modality for a longitudinal view, and an imaging modality for an angiography view.

4. The imaging device of claim 3, wherein:
a first imaging modality of the multiple imaging modalities is the OCT imaging modality configured to output the tomography image of a lumen or the OCT image of a lumen; and
at least a second imaging modality of the multiple imaging modalities is one or more of the following: a near-infrared fluorescence (NIRF) image modality, a near-infrared auto-fluorescence (NIRAF) imaging modality, a near-infrared fluorescence (NIRF) imaging modality in a carpet view, a near-infrared auto-fluorescence (NIRAF) imaging modality in a carpet view, an imaging modality for a three-dimensional (3D) rendering, an imaging modality for a 3D rendering of a vessel, an imaging modality for a 3D rendering of a vessel in a half-pipe view or display, an imaging modality for a lumen profile, an imaging modality for a lumen diameter display, an imaging modality for a longitudinal view, an imaging modality for an anatomical view, and an imaging modality for an angiography view.

5. The imaging device of claim 3, wherein one or more of the following:
(i) a first imaging modality of the multiple imaging modalities shows an OCT image and NIRF and/or NIRAF data, the NIRF and/or NIRAF data displayed in a circle around an outer edge of the OCT image; and/or
(ii) at least a second imaging modality, which is at least one of the multiple imaging modalities other than a first imaging modality of the multiple imaging modalities, shows or is a cross-sectional, longitudinal view and/or the three-dimensional rendering.

6. The imaging device of claim 5, wherein one or more of the following:
(i) a first control bar or tool displayed in or with an image of the first imaging modality is a rotational, circular or semi-circular, and/or rotatable control bar or tool with two handle bars defining endpoints that bound color extremes of the NIRF and/or NIRAF data and/or defining a cut or area of the image displayed by the first imaging modality, the cut or area is to be depicted in the at least the second imaging modality, and the first control bar or tool operates to be moved bi-directionally in a circular rotation according to the input request;
(ii) a first control bar or tool is displayed such that the first control bar or tool is angled at a predetermined or set angle with respect to an image of the first imaging modality;
(iii) a first control bar or tool is displayed such that the first control bar or tool is angled at one of −45 degrees, 45 degrees, −50 degrees, 50 degrees, −55 degrees, 55 degrees, 40 degrees, −40 degrees, or the predetermined or set angle with respect to an image of the first imaging modality;
(iv) the one or more processors further operate to display an image of the first imaging modality with or without a control bar or tool; and/or
(v) the one or more control bars or tools operate to one or more of the following: define a dimension of one or more of the displayed images, define a range of data shown in one or more of the displayed images, and/or correspond to data in a profile shown in one or more of the displayed images.

7. The imaging device of claim 5, wherein one or more of the following:
(i) a first control bar or tool configured to be displayed in or with an image of the first imaging modality is a rotatable control bar or tool with two handle bars, the two handle bars designating an area of the image of the first imaging modality to be displayed in the at least one of the multiple imaging modalities other than the first imaging modality;
(ii) at least the second imaging modality of the multiple imaging modalities shows NIRF and/or NIRAF data displayed in a carpet view;
(iii) a second control bar or tool of the one or more control bars or tools is displayed on half of the carpet view matching a corresponding area designated by a first control bar or tool in or on an image of the at least first imaging modality, the second control bar or tool having two handles and operating to be moved bi-directionally, the bi-directional movement being one of rotational, horizontal, vertical, parallel, or perpendicular to the one or more control bars or tools, or along the one or more control bars or tools, wherein the second control bar or tool is synchronized with, interacts with, or corresponds to, the first control bar or tool;
(iv) a NIRF and/or NIRAF signal gauge is displayed with the second imaging modality to highlight a NIRF and/or NIRAF signal intensity; and/or
(v) the NIRF and/or NIRAF signal gauge highlights a maximum NIRF and/or NIRAF signal intensity using an arrow.

8. The imaging device of claim 5, wherein one or more of the following:
(i) a third imaging modality of the multiple imaging modalities shows an image of a three-dimensional (3D) view of a half pipe vessel;
(ii) the NIRF and/or NIRAF data is displayed on an inner wall of the half pipe vessel shown in the third imaging modality; and/or
(iii) a third control bar or tool of the one or more control bars or tools is displayed on the 3D view of the half pipe vessel matching a corresponding area designated by a first control bar or tool in or on the at least first imaging modality, the third control bar or tool having two handles and operating to be moved bi-directionally, the bi-directional movement being one of rotational, horizontal, vertical, parallel, or perpendicular to the one or more control bars or tools, or along the one or more control bars or tools, wherein the third control bar or tool is synchronized with, interacts with, or corresponds to, the first control bar or tool.

9. The imaging device of claim 5, wherein one or more of the following:
(i) a fourth imaging modality of the multiple imaging modalities shows an image of an anatomical view or an angiography view;
(ii) NIRF and/or NIRAF data is displayed along a vessel shown in the anatomical view or the angiography view of the fourth imaging modality; and/or
(iii) a fourth control bar or tool of the one or more control bars or tools is displayed on the anatomical view or the angiography view matching a corresponding area designated by a first control bar or tool in or on the at least first imaging modality, the fourth control bar or tool appearing horizontally along the vessel, wherein the fourth control bar or tool is synchronized with, interacts with, or corresponds to, the first control bar or tool.

10. The imaging device of claim 5, wherein a second imaging modality shows a lumen diameter or a lumen profile displayed with the tomography image or the OCT image.

11. The imaging device of claim 5, wherein, in response to a first control bar or tool being moved or changed for the first imaging modality and/or in response to a second control bar or tool being moved or changed for one of the imaging modalities other than the first imaging modality, the one or more processors operate to:
  detect a catheter circumference, find a center of the catheter or catheter circumference, and draw a dot at the center of the catheter or catheter circumference in an image of the first imaging modality;
  draw a line that passes through the dot at the catheter center or the catheter circumference center and that connects two points on an edge or edges of a circle of the tomographic image or the OCT image to create a diagonal line at one of −45 degrees, 45 degrees, −50 degrees, 50 degrees, −55 degrees, 55 degrees, 40 degrees, −40 degrees, or a predetermined or set angle with respect to the tomographic image or the OCT image to create a semi-circle around the tomographic image or the OCT image, where an arc of the semi-circle represents half of the longitudinal cross-sectional view;
  determine active imaging modalities among the multiple imaging modalities; and
  calculate a new orientation/position of the one or more control bars or tools and the active imaging modalities.

12. The imaging device of claim 11, wherein, in response to the one or more processors finishing the calculation of the new orientation/position of the one or more control bars or tools and determining the active imaging modalities, the one or more processors further operate to:
  update the one or more control bars or tools within each imaging modality of the multiple imaging modalities;
  update any NIRF and/or NIRAF data and change its corresponding display;
  update a second imaging modality to scroll vertically and update any related NIRF and/or NIRAF data and its corresponding display;
  update a third imaging modality to scroll vertically and update a corresponding three-dimensional (3D) half pipe vessel view with NIRF and/or NIRAF data overlaid on the vessel; and
  update a NIRF and/or NIRAF gauge by re-positioning an arrow to highlight a greatest or maximum NIRF and/or NIRAF signal intensity matching to the selected portion of the NIRF and/or NIRAF data or ring.

13. The imaging device of claim 1, further comprising a touch screen, wherein the one or more processors further operate to one or more of the following:
  detect a selected region of interest, via an input received through or with the touch screen;
  detect a single press/touch and drag with a finger or tool of a user over an area of the touch screen to move a semi-circle of the at least one imaging modality view or image or to move the at least one imaging modality view or image, and calculate and update a new orientation/position of the at least one imaging modality view or image based upon a release of the single press/touch by the finger or tool of the user;
  detect two simultaneous touch points made on the at least one imaging modality view or image and redraw the image of the at least one imaging modality such that a control bar or tool having two handles defines the redrawn image where both of the two handles align near or on an arc of the redrawn image based on the two touch points, and calculate and update the new orientation/position of the at least one imaging modality image or view based upon a release of the two touch points; and/or
  detect two simultaneous touch points, made by fingers or tools of the user, made on the at least one imaging modality showing a tomographic image or an Optical Coherence Tomography (OCT) image, where the fingers or the tools are held in place, and the two touch points are swept around the tomographic image or the OCT image in a circular motion that moves a rotational control bar displayed on the at least one imaging modality, and calculate and update the new orientation/position of the at least one imaging modality image or view based upon a release of the two touch points.

14. A method for controlling, viewing and/or updating data of multiple imaging modalities in a display, the method comprising:
  displaying an image for each of multiple imaging modalities on the display;
  receiving an input request during a rotational, scrolling, or sliding movement of an interaction, performed on or performed using the display, with one or more of the displayed images where at least the display of the one or more images is changed during the interaction, and/or receiving an input request during an interaction, performed on or performed using the display, with one or more moveable control bars or tools displayed on or in the one or more of the displayed images where the one or more moveable control bars or tools are rotationally moved or are scrolled or slid during the interaction to receive the input request, the input request operating to change the one or more of the displayed images of at least one of the multiple imaging modalities; and
  synchronously updating each displayed image for each of the multiple imaging modalities based on the received input request such that data is changed in each of the displays for each of the multiple imaging modalities based on the received input request and such that: (i) an orientation or position for each displayed image(s) for each of the other multiple imaging modalities is updated synchronously by rotating, scrolling, or sliding each of the displayed image(s) by an amount equal or corresponding to the rotational, scrolling, or sliding movement of the interaction and/or the moveable control bars or tools and displayed using the updated orientation or position based on the rotational, scrolling, or sliding movement of the interaction and/or the moveable control bars or tools, or (ii) a frame for each displayed image(s) for each of the other multiple imaging modalities is updated synchronously to be a different frame corresponding to or located at a position selected by the scrolling or sliding along a direction of an image of the one or more images where the movement is a scrolling or sliding movement and/or where the moveable control bars or tools are scrolled or slid,
wherein at least:
(i) the method further comprises determining whether at least one of two cases occurs, where a first case of the two cases is where the input request is received during the rotational, scrolling, or sliding movement of the interaction with a displayed image for one imaging modality of the multiple imaging modalities, and where a second case of the two cases is where the input request is received during the interaction with one or more rotational, scrolling, or sliding moveable control bars or tools displayed on or in the displayed image for the one imaging modality of the multiple imaging modalities, and, where the first case and/or the second case of the two cases is/are determined to occur, the synchronous update is performed for the other displayed image(s) for each of the multiple imaging modalities; and (ii) the method further comprises determining whether at least one of two other cases occurs, where a first other case of the two other cases is where the input request is received during the rotational, scrolling, or sliding movement of the interaction with a displayed image for another imaging modality of the multiple imaging modalities and where a second other case of the two other cases is where the input request is received during the interaction with one or more rotational, scrolling, or sliding moveable control bars or tools displayed on or in the displayed image for the another imaging modality of the multiple imaging modalities, and, where the first other case and/or the second other case of the two other cases is/are determined to occur, the synchronous update is performed for the other displayed image(s) for each of the multiple imaging modalities, where the one imaging modality is different from the another imaging modality.

15. The method of claim 14, further comprising one or more of the following:

(i) updating all of the multiple imaging modalities based on a specific moment in time based on when the input request is received or based on when the input request is selected or entered by a user;

(ii) displaying a control bar or tool of the one or more control bars or tools on or in at least a first imaging modality of the multiple imaging modalities, and detecting the input request based on a change performed to the control bar or tool, the control bar or tool operating to move bi-directionally, the bi-directional movement being one of rotational, horizontal, vertical, parallel, or perpendicular to the control bar or tool or to the one or more control bars or tools, or along the control bar or tool or the one or more control bars or tools;

(iii) displaying the one or more control bars or tools, where each control bar of the one or more control bars or tools is displayed on a respective imaging modality of the multiple imaging modalities, and to detect the input request based on a change performed to one of the control bars or tools, the one or more control bars or tools operating to move bi-directionally, the bi-directional movement being one of rotationally, horizontal, vertical, parallel, or perpendicular to the control bar or tool or to the one or more control bars or tools, or along the control bar or tool or the one or more control bars or tools;

(iv) one or more of: detecting stent expansion or underexpansion, detecting stent apposition or malapposition, performing co-registration of two or more imaging modalities of the multiple imaging modalities, performing imaging using at least one of the multiple imaging modalities, displaying a notification regarding the detected stent expansion or underexpansion, and displaying a notification regarding the detected stent apposition or malapposition;

(v) displaying the one or more control bars or tools such that each control bar or tool of the one or more control bars or tools is displayed on or in an image for a respective imaging modality of the multiple imaging modalities and/or such that all displayed images for the multiple imaging modalities include a control bar or tool displayed on or in each respective displayed image of the displayed images, and to detect the input request based on a change performed to one of the one or more control bars or tools; and/or (vi) performing the synchronous update such that the input request operates to change two-dimensional (2D) and three-dimensional (3D) aspects or features in one or more images of the multiple imaging modalities.

16. The method of claim 15, wherein one or more of the following:

(i) the multiple imaging modalities include two or more of the following modalities: an imaging modality for a tomography image, an imaging modality for an Optical Coherence Tomography (OCT) image, an imaging modality for an OCT image of a lumen, an imaging modality for a near-infrared fluorescence (NIRF) image, an imaging modality for a near-infrared auto-fluorescence (NIRAF) image, an imaging modality for a near-infrared auto-fluorescence (NIRAF) image of a lumen, a near-infrared fluorescence (NIRF) imaging modality in a carpet view, a near-infrared auto-fluorescence (NIRAF) imaging modality in a carpet view, an imaging modality for a three-dimensional (3D) rendering, an imaging modality for a 3D rendering of a vessel or lumen, an imaging modality for a 3D rendering of a vessel in a half-pipe view or display, an imaging modality for a lumen profile, an imaging modality for a lumen diameter view or display, an imaging modality for a longitudinal view, and an imaging modality for an angiography view;

(ii) the display device displays the images of the multiple imaging modalities as one or more of the following: a tomography image of a lumen, an Optical Coherence Tomography (OCT) image of a lumen, a near-infrared auto-fluorescence (NIRAF) image of a lumen, a near-infrared auto-fluorescence (NIRAF) image of a lumen in a carpet view, a near-infrared fluorescence (NIRF) image of a lumen, a near-infrared fluorescence (NIRF) image of a lumen in a carpet view, a three-dimensional (3D) rendering of a lumen, a 3D rendering of a vessel, a 3D rendering of a vessel in a half-pipe view, a lumen profile view, a lumen diameter view, a longitudinal cross-sectional view of a lumen, and an angiography view of a lumen;

(iii) the multiple imaging modalities include three or more of the following modalities: an imaging modality for a tomography image, an Optical Coherence Tomography (OCT) image modality, a near-infrared fluorescence (NIRF) image modality, a near-infrared auto-fluorescence (NIRAF) imaging modality, a near-infrared fluorescence (NIRF) imaging modality in a carpet view, a near-infrared auto-fluorescence (NIRAF) imaging modality in a carpet view, an imaging modality for a three-dimensional (3D) rendering, an imaging modality for a 3D rendering of a vessel, an imaging modality for a 3D rendering of a vessel in a half-pipe view or display, an imaging modality for a lumen profile, an imaging modality for a lumen diameter display, an imaging modality for a longitudinal view, and an imaging modality for an angiography view; and/or (iv) the multiple imaging modalities include four or more of the following modalities: an imaging modality for a tomography image, an Optical Coherence Tomography (OCT) image modality, a near-infrared fluorescence (NIRF) image modality, a near-infrared auto-fluorescence (NIRAF) imaging modality, a near-infrared fluorescence (NIRF) imaging modality in a carpet view, a near-infrared auto-fluorescence (NIRAF) imaging modality in a carpet view, an imaging modality for a three-dimensional (3D) rendering, an imaging modality for a 3D rendering of a vessel, an imaging modality for a 3D rendering of a vessel in a half-pipe view or display, an imaging modality for a lumen profile, an imaging modality for a lumen diameter display, an imaging modality for a longitudinal view, and an imaging modality for an angiography view.

17. The method of claim 16, wherein:
a first imaging modality of the multiple imaging modalities is an imaging modality for the tomography image or the OCT image; and
at least a second imaging modality of the multiple imaging modalities is one or more of the following: an imaging modality for a near-infrared fluorescence (NIRF) image, a near-infrared auto-fluorescence (NIRAF) imaging modality, a near-infrared fluorescence (NIRF) imaging modality in a carpet view, a near-infrared auto-fluorescence (NIRAF) imaging modality in a carpet view, an imaging modality for a three-dimensional (3D) rendering, an imaging modality for a 3D rendering of a vessel, an imaging modality for a 3D rendering of a vessel in a half-pipe view or display, an imaging modality for a lumen profile, an imaging modality for a lumen diameter view or display, an imaging modality for a longitudinal view, an imaging modality for a longitudinal cross-sectional view, an imaging modality for an anatomical view, an imaging modality for an anatomical view of a vessel or lumen, and an imaging modality for an angiography view.

18. The method of claim 16, wherein one or more of the following:
(i) a first imaging modality of the multiple imaging modalities shows an OCT image and NIRF and/or NIRAF data, the NIRF and/or NIRAF data displayed in a circle around an outer edge of the OCT image; and/or
(ii) at least a second imaging modality, which is at least one of the multiple imaging modalities other than a first imaging modality of the multiple imaging modalities, shows or is a cross-sectional, longitudinal view and/or a three-dimensional rendering.

19. The method of claim 18, wherein one or more of the following:
(i) a first control bar or tool displayed in or with an image of the first imaging modality is a rotational, circular or semi-circular, and/or rotatable control bar or tool with two handle bars, the two handle bars defining endpoints that bound color extremes of the NIRF and/or NIRAF data and/or defining a cut or area of the image displayed by the first imaging modality, the cut or area is to be depicted in at least the second imaging modality, and the first control bar or tool operates to be moved bi-directionally in a circular rotation according to the input request;
(ii) a first control bar or tool is displayed such that the first control bar or tool is angled at a predetermined or set angle with respect to an image of the first imaging modality;
(iii) a first control bar or tool is displayed such that the first control bar or tool is angled at one of −45 degrees, 45 degrees, −50 degrees, 50 degrees, −55 degrees, 55 degrees, 40 degrees, −40 degrees, or the predetermined or set angle with respect to an image of the first imaging modality;
(iv) an image of the first imaging modality is displayed with or without a control bar or tool; and/or
(v) the one or more control bars or tools operate to one or more of the following: define a dimension of one or more of the displayed images, define a range of data shown in one or more of the displayed images, and/or correspond to data in a profile shown in one or more of the displayed images.

20. The method of claim 18, wherein one or more of the following:
(i) a first control bar or tool configured to be displayed in or with an image of the first imaging modality is a rotatable control bar or tool with two handle bars, the two handle bars designating an area of the image of the first imaging modality to be displayed in the at least one of the multiple imaging modalities other than the first imaging modality;
(ii) at least the second imaging modality of the multiple imaging modalities shows NIRF and/or NIRAF data displayed in a carpet view;
(iii) a second control bar or tool of the one or more control bars or tools is displayed on half of the carpet view matching a corresponding area designated by a first control bar or tool in or on an image of the at least first imaging modality, the second control bar or tool having two handles and operating to be moved bi-directionally, the bi-directional movement being one of rotational, horizontal, vertical, parallel, or perpendicular to the one or more control bars or tools, or along the one or more control bars or tools, wherein the second control bar or tool is synchronized with, interacts with, or corresponds to, the first control bar or tool;
(iv) a NIRF and/or NIRAF signal gauge is displayed with the second imaging modality to highlight a NIRF and/or NIRAF signal intensity; and/or
(v) the NIRF and/or NIRAF signal gauge highlights a maximum NIRF and/or NIRAF signal intensity using an arrow.

21. The method of claim 18, wherein one or more of the following:
(i) a third imaging modality of the multiple imaging modalities shows an image of a three-dimensional (3D) view of a half pipe vessel;
(ii) the NIRF and/or NIRAF data is displayed on an inner wall of the half pipe vessel shown in the third imaging modality; and/or
(iii) a third control bar or tool of the one or more control bars or tools is displayed on the 3D view of the half pipe vessel matching a corresponding area designated by a first control bar or tool in or on the at least first imaging modality, the third control bar or tool having two handles and operating to be moved bi-directionally, the bi-directional movement being one of rotationally, horizontal, vertical, parallel, or perpendicular to the one or more control bars or tools, or along the one or more control bars or tools, wherein the third control bar or tool is synchronized with, interacts with, or corresponds to, the first control bar or tool.

22. The method of claim 18, wherein one or more of the following:
(i) a fourth imaging modality of the multiple imaging modalities shows an image of an anatomical view or an angiography view;
(ii) NIRF and/or NIRAF data is displayed along a vessel shown in the anatomical view or the angiography view of the fourth imaging modality; and/or
(iii) a fourth control bar or tool of the one or more control bars or tools is displayed on the anatomical view or the angiography view matching a corresponding area designated by a first control bar or tool in or on the at least first imaging modality, the fourth control bar or tool appearing horizontally along the vessel, wherein the fourth control bar or tool is synchronized with, interacts with, or corresponds to, the first control bar or tool.

23. The method of claim 18, wherein a second imaging modality shows a lumen diameter or a lumen profile displayed with the tomography image or the OCT image.

24. The method of claim 18, in response to a first control bar or tool being moved or changed for the first imaging modality and/or in response to a second control bar or tool being moved or changed for one of the imaging modalities other than the first imaging modality, further comprising:
detecting a catheter circumference, finding a center of the catheter or the catheter circumference, and drawing a dot at the center of the catheter or the catheter circumference in an image of the first imaging modality;
drawing a line that passes through the dot at the catheter center or the catheter circumference center and that connects two points on an edge or edges of a circle of the tomographic image or the OCT image to create a diagonal line at one of −45 degrees, 45 degrees, −50 degrees, 50 degrees, −55 degrees, 55 degrees, 40 degrees, −40 degrees, or a predetermined or set angle with respect to the tomographic image or the OCT image to create a semi-circle around the tomographic image or the OCT image, where an arc of the semi-circle represents half of the longitudinal cross-sectional view;
determining active imaging modalities among the multiple imaging modalities; and
calculating a new orientation/position of the one or more control bars or tools and the active imaging modalities.

25. The method of claim 24, in response to completion of the calculation step of the new orientation/position of the one or more control bars or tools and the determining step for the active imaging modalities, further comprising:
updating the one or more control bars or tools within each imaging modality of the multiple imaging modalities;
updating any NIRF and/or NIRAF data and change its corresponding display;
updating a second imaging modality to scroll vertically and update any related NIRF and/or NIRAF data and its corresponding display;
updating a third imaging modality to scroll vertically and update a corresponding three-dimensional (3D) half pipe vessel view with NIRF and/or NIRAF data overlaid on the vessel; and
updating a NIRF and/or NIRAF gauge by re-positioning an arrow to highlight a greatest or maximum NIRF and/or NIRAF signal intensity matching to the selected portion of the NIRF and/or NIRAF data or ring.

26. The method of claim 14, further comprising, via a touch screen:
detecting a selected region of interest, via an input received through or with the touch screen;
detecting a single press/touch and drag with a finger or tool of a user over an area of the touch screen to move a semi-circle of the at least one imaging modality view or image or to move the at least one imaging modality view or image, and calculating and updating a new orientation/position of the at least one imaging modality view or image based upon a release of the single press/touch by the finger or tool of the user;
detecting two simultaneous touch points made on the at least one imaging modality view or image and redraw the image of the at least one imaging modality such that a control bar or tool having two handles defines the redrawn image where both of the two handles align near or on an arc of the redrawn image based on the two touch points, and calculating and updating the new orientation/position of the at least one imaging modality image or view based upon a release of the two touch points; and/or
detecting two simultaneous touch points, made by fingers or tools of the user, made on the at least one imaging modality showing a tomographic image or an Optical Coherence Tomography (OCT) image, where the fingers or the tools are held in place, and the two touch points are swept around the tomographic image or the OCT image in a circular motion that moves a rotational control bar displayed on the at least one imaging modality, and calculating and updating the new orientation/position of the at least one imaging modality image or view based upon a release of the two touch points.

27. A non-transitory computer-readable storage medium storing at least one program for causing a computer to execute a method for controlling, viewing and/or updating data of multiple imaging modalities in a display, the method comprising:
displaying an image for each of multiple imaging modalities on the display;
receiving an input request during a rotational, scrolling, or sliding movement of an interaction, performed on or performed using the display, with one or more of the displayed images where at least the display of the one or more images is changed during the interaction, and/or receiving an input request during an interaction, performed on or performed using the display, with one or more moveable control bars or tools displayed on or in the one or more of the displayed images where the one or more moveable control bars or tools are rotationally moved or are scrolled or slid during the interaction to receive the input request, the input request operating to change the one or more of the displayed images of at least one of the multiple imaging modalities; and
synchronously updating each displayed image for each of the multiple imaging modalities based on the received input request such that data is changed in each of the displays for each of the multiple imaging modalities based on the received input request and such that: (i) an orientation or position for each displayed image(s) for each of the other multiple imaging modalities is updated synchronously by rotating, scrolling, or sliding each of the displayed image(s) by an amount equal or corresponding to the rotational, scrolling, or sliding movement of the interaction and/or the moveable control bars or tools and displayed using the updated orientation or position based on the rotational, scrolling, or sliding movement of the interaction and/or the moveable control bars or tools, or (ii) a frame for each displayed image(s) for each of the other multiple imaging modalities is updated synchronously to be a different frame corresponding to or located at a position selected by the scrolling or sliding along a direction of an image of the one or more images where the movement is a scrolling or sliding movement and/or where the moveable control bars or tools are scrolled or slid, wherein at least:

(i) the method further comprises determining whether at least one of two cases occurs, where a first case of the two cases is where the input request is received during the rotational, scrolling, or sliding movement of the interaction with a displayed image for one imaging modality of the multiple imaging modalities and where a second case of the two cases is where the input request is received during the interaction with one or more rotational, scrolling, or sliding moveable control bars or tools displayed on or in the displayed image for the one imaging modality of the multiple imaging modalities, and, where the first case and/or the second case of the two cases is/are determined to occur, the synchronous update is performed for the other displayed image(s) for each of the multiple imaging modalities; and (ii) the method further comprises determining whether at least one of two other cases occurs, where a first other case of the two other cases is where the input request is received during the rotational, scrolling, or sliding movement of the interaction with a displayed image for another imaging modality of the multiple imaging modalities and where a second other case of the two other cases is where the input request is received during the interaction with one or more rotational, scrolling, or sliding moveable control bars or tools displayed on or in the displayed image for the another imaging modality of the multiple imaging modalities, and, where the first other case and/or the second other case of the two other cases is/are determined to occur, the synchronous update is performed for the other displayed image(s) for each of the multiple imaging modalities, where the one imaging modality is different from the another imaging modality.

* * * * *